(12) United States Patent
Wang

(10) Patent No.: US 11,607,513 B2
(45) Date of Patent: Mar. 21, 2023

(54) SUCTION DEVICES FOR MEDICAL DEVICES AND MEDICAL DEVICE SYSTEMS INCLUDING SUCTION DEVICES

(71) Applicant: NEVAP, INC., San Jose, CA (US)

(72) Inventor: Benjamin Wang, San Jose, CA (US)

(73) Assignee: NEVAP, INC., San Jose, CA (US)

( * ) Notice: Subject to any disclaimer, the term of this patent is extended or adjusted under 35 U.S.C. 154(b) by 886 days.

(21) Appl. No.: 16/341,372

(22) PCT Filed: Oct. 12, 2017

(86) PCT No.: PCT/US2017/056393
§ 371 (c)(1),
(2) Date: Apr. 11, 2019

(87) PCT Pub. No.: WO2018/071705
PCT Pub. Date: Apr. 19, 2018

(65) Prior Publication Data
US 2020/0054799 A1 Feb. 20, 2020

Related U.S. Application Data

(60) Provisional application No. 62/407,080, filed on Oct. 12, 2016.

(51) Int. Cl.
*A61M 16/04* (2006.01)
*A61B 18/00* (2006.01)
(Continued)

(52) U.S. Cl.
CPC ......... *A61M 16/0463* (2013.01); *A61B 18/00* (2013.01); *A61M 1/84* (2021.05);
(Continued)

(58) Field of Classification Search
CPC ................ A61M 1/84; A61M 16/0447; A61M 16/0463; A61M 16/0465; A61M 25/007;
(Continued)

(56) References Cited

U.S. PATENT DOCUMENTS 3,583,404 A  6/1971  McWhorter
3,995,643 A  12/1976 Merav
(Continued)

FOREIGN PATENT DOCUMENTS

CN  202699807 U  1/2013
CN  203763615 U  8/2014
(Continued)

OTHER PUBLICATIONS

Covidien, TaperGuard Endotracheal and Specialty Tubes, 2014,Date Retrieved Oct. 29, 2 pages.
(Continued)

*Primary Examiner* — Amber R Stiles
(74) *Attorney, Agent, or Firm* — Resonance IP Law, PC

(57) ABSTRACT

A suction device for use with a medical device may include a suction device body and an extension. The suction device body may include a first lumen positioned therein and including a plurality of holes. The extension may include a second lumen positioned therein and may be coupled to the suction device body and configured to facilitate connection of the suction device body to a suction line. The second lumen may be in communication with/open to the first lumen and the suction line may be adapted for connection to a pump configured to apply a negative pressure to the first and second lumens. The suction device may evacuate fluids and/or solids from a patient in an area proximate to the suction device.

17 Claims, 18 Drawing Sheets

(51) Int. Cl.
*A61M 1/00* (2006.01)
*A61M 25/00* (2006.01)
*A61M 25/01* (2006.01)

(52) U.S. Cl.
CPC .... *A61M 16/0447* (2014.02); *A61M 16/0465* (2013.01); *A61B 2018/00577* (2013.01); *A61B 2218/007* (2013.01); *A61M 25/007* (2013.01); *A61M 25/0108* (2013.01); *A61M 2205/0205* (2013.01)

(58) Field of Classification Search
CPC ...... A61M 25/0108; A61M 2205/0205; A61M 16/0409; A61M 16/0479; A61M 16/0484; A61M 2205/0238; A61M 2205/0222; A61M 1/80; A61M 25/0029; A61M 2205/32; A61B 18/00; A61B 2018/00577; A61B 2218/007
See application file for complete search history.

(56) References Cited

U.S. PATENT DOCUMENTS

| | | | |
|---|---|---|---|
| 4,278,081 A | 7/1981 | Jones | |
| 4,327,721 A * | 5/1982 | Goldin | A61M 16/0486 128/207.15 |
| 4,437,856 A | 3/1984 | Valli | |
| 4,693,243 A | 9/1987 | Buras | |
| 4,840,173 A | 6/1989 | Porter, III | |
| 4,973,305 A | 11/1990 | Golzer | |
| 5,146,916 A | 9/1992 | Catalani | |
| 5,311,864 A | 5/1994 | Huerta | |
| 5,389,074 A | 2/1995 | Parker et al. | |
| 5,501,215 A | 3/1996 | Huerta | |
| 5,513,627 A | 5/1996 | Flam | |
| 5,715,816 A | 2/1998 | Mainiero et al. | |
| 5,819,723 A | 10/1998 | Joseph | |
| 6,048,332 A | 4/2000 | Duffy | |
| 6,460,540 B1 * | 10/2002 | Klepper | A61M 16/0463 128/207.14 |
| 7,669,600 B2 | 3/2010 | Morejon | |
| 8,196,584 B2 | 6/2012 | Maguire | |
| 8,357,118 B2 | 1/2013 | Orr | |
| 8,535,265 B2 | 9/2013 | Burnett et al. | |
| 9,327,091 B2 | 5/2016 | Wang et al. | |
| 9,446,213 B2 | 9/2016 | Wang | |
| 9,579,475 B2 | 2/2017 | Wang | |
| 10,071,212 B1 | 9/2018 | Riesberg | |
| 2004/0116898 A1 | 6/2004 | Hawk | |
| 2004/0255951 A1 | 12/2004 | Grey | |
| 2008/0011304 A1 | 1/2008 | Stewart | |
| 2008/0172120 A1 | 7/2008 | Fenn et al. | |
| 2009/0260632 A1 | 10/2009 | Abnousi et al. | |
| 2010/0051035 A1 * | 3/2010 | Jenkins | A61M 16/0479 128/207.15 |
| 2010/0147309 A1 | 6/2010 | Cuevas et al. | |
| 2010/0269830 A1 | 10/2010 | Layer et al. | |
| 2011/0023884 A1 | 2/2011 | Cuevas et al. | |
| 2011/0139159 A1 | 6/2011 | Nelson | |
| 2012/0000471 A1 | 1/2012 | Harrington et al. | |
| 2012/0022380 A1 | 1/2012 | Chernomorsky | |
| 2012/0024293 A1 | 2/2012 | Maguire et al. | |
| 2012/0143006 A1 | 6/2012 | Avitsian et al. | |
| 2012/0215198 A1 | 8/2012 | Cheney | |
| 2013/0060273 A1 | 3/2013 | Fogarty et al. | |
| 2013/0112207 A1 | 5/2013 | Roth | |
| 2013/0190706 A1 | 7/2013 | Kleiner | |
| 2014/0033455 A1 | 2/2014 | Vazales et al. | |
| 2014/0343366 A1 * | 11/2014 | Coe | A61M 1/85 600/205 |
| 2015/0101598 A1 | 4/2015 | Wang et al. | |
| 2015/0101611 A1 | 4/2015 | Wang | |
| 2015/0101612 A1 | 4/2015 | Wang | |
| 2015/0209535 A1 | 7/2015 | Cole et al. | |

FOREIGN PATENT DOCUMENTS

| | | |
|---|---|---|
| CN | 203763616 U | 8/2014 |
| DE | 202009016034 U1 | 3/2010 |
| EP | 1889636 A1 | 2/2008 |
| WO | 9321816 A1 | 11/1993 |
| WO | 9640339 A1 | 12/1996 |
| WO | 2007130579 A2 | 11/2007 |
| WO | 2012087837 A1 | 6/2012 |
| WO | 2015042607 A1 | 3/2015 |

OTHER PUBLICATIONS

International Search Report and Written Opinion of the International Searching Authority, Patent Cooperation Treaty (dated Jan. 16, 2018), PCT/US2017/056393, 15 pgs.

International Search Report and Written Opinion of the International Searching Authority, Patent Cooperation Treaty (dated Jan. 28, 2015), PCT/US2014/059958, 13 pgs.

Kimberly-Clark Worldwide, Inc, KIMVENT Closed Suction Systems, Date Retrieved Oct. 29, 2014, 4 pages.

Smiths Medical, SACETT Suction Above Cuff ET Tube, Date Retrieved Oct. 29, 2014, 9 pages.

Teleflex, Inc, Teleflex ISIS HVT, the First Convertible Endotracheal Tube, Date Retrieved Oct. 29, 2014, 2 pages.

European Extended Search Report dated May 12, 2020 for European Application No. 17860330.4.

* cited by examiner

SUCTION DEVICES FOR MEDICAL DEVICES AND MEDICAL DEVICE SYSTEMS INCLUDING SUCTION DEVICES

RELATED APPLICATION

This application is a NON-PROVISIONAL of, and claims priority to, U.S. Provisional Patent Application No. 62/407,080 entitled "SUCTION DEVICES FOR MEDICAL DEVICES AND MEDICAL DEVICE SYSTEMS INCLUDING SUCTION DEVICES" filed Oct. 12, 2016, which is incorporated by reference, in its entirety, herein.

TECHNICAL FIELD

This specification generally relates to the field of medical devices and, more specifically to suction devices for medical devices such as tracheal tubes, ablation tools, laryngeal mask airway systems, and tracheostomy tube systems.

BACKGROUND

Tracheal tubes with inflatable balloons with suction means are broadly known in the prior art. However, the suctioning means of such prior arts are inefficient with suctioning secretions above and around the balloon, therefore allowing secretions and/or pathogens to travel through the balloon and tracheal walls and into the airflow of the tracheal tube. In certain situations, the secretions/pathogens get aerosolized by the high velocity of the ventilated air traveling through the tracheal tube and into the patient's lungs. Aerosolized pathogens traveling at high velocity may send the pathogens deep into the lungs, which may cause ventilator associated pneumonia (VAP) as well as other diseases.

SUMMARY

Suction devices and medical device systems that incorporate or otherwise use a suction device are herein disclosed. Exemplary suction devices include a suction device body and an extension. The suction device body may include a first lumen positioned therein and a plurality of holes. The holes may be on and/or through any surface or sidewall of the suction device body. For example, the holes may be on the top, bottom, and/or side of the suction device body. In instances where there are holes on the top and bottom of the suction device body, the holes on the top may align with the holes on the bottom of the suction device body and/or may be asymmetrically placed.

The suction devices and/or suction device bodies disclosed herein may be any appropriate shape including, but not limited to, a curved, circular, and semi-circular shape. In some instances, a shape, size, and/or positioning of the suction device in the medical device system may be adapted to correspond with a component of the medical device system. For example, a shape of the suction device and/or suction device body may be configured to correspond with a tube or handle of a medical device system.

In some embodiments the suction device body may include one or structural elements positioned within and/or around the first lumen that may act to, for example, maintain the opening of the first lumen when a solid and/or liquid flows through the first lumen.

The extension may be coupled to, extend from, and/or be part of the suction device body and may include a second lumen positioned therein. The second lumen may be in communication with and/or open to the first lumen. In some instances, the extension may extend substantially orthogonally from an exterior surface of the suction device body. The extension may be configured to facilitate connection of the suction device body to a suction line that includes a third lumen in communication with and/or open to the second lumen. In some instances, the extension may include a structural element (e.g., a clip or screw component) configured to facilitate attachment of suction device body to the suction line.

The suction line may be adapted for connection to a pump (e.g., a suction pump) configured to apply a negative pressure to the first, second, and third lumens. At times, the suction device is adapted to facilitate continuous or periodic application of negative pressure to, for example, tissue of a patient proximate to the suction device/suction device body. The continuous or periodically applied negative pressure may be provided by the suction pump via the first, second, and/or third lumens. In some instances, the suction line may be coupled to a medical device such as, but not limited to, a tracheal tube system, an ablation tool system, a laryngeal mask airway system, and a tracheostomy tube system and the suction device, suction device body, and/or extension may be invaginated into the suction line and/or a medical device the suction line is coupled to the medical device in order to, for example, reduce the profile of the medical device.

One or more of the plurality of holes may be adapted to allow the flow of a solid, liquid, and/or gas from outside the suction device body into the first lumen responsively to the application of negative pressure by the pump to the first lumen via the second lumen, third lumen, and/or suction line. In many instances, the flow of the solid, liquid, and/or gas will be from tissue of a patient or from a surgical or respiratory field proximate to the suction device.

In some instances, some, or all, of the holes of the suction device body may be smaller in diameter or overall size than that of the first lumen, second lumen, and/or third lumen so that, for example, a solid or semi-solid device sucked into a particular hole will be smaller than the first, second, and/or third lumen(s) and, therefore, will not occlude the respective lumen(s) as it is evacuated away from outside the suction device. Also, an occlusion of one or more holes will not substantially inhibit the ability of the suction device to evacuate fluids, semi-solids, and/or solids from a site (e.g., a patient's throat, trachea, mouth, or surgical incision) in which the suction device is being used because there are other holes in the suction device body that are providing the negative pressure to the site.

At times, the suction device may adapted so that the negative pressure applied to the suction line is atraumatically applied to tissue of a patient that is proximate to the suction device and/or a medical device coupled to, or in communication with, the suction device. Atraumatic application of negative pressure to the tissue may be achieved by, for example, spreading the force of the negative pressure across the plurality of holes so that, for example, the force of the negative pressure provided by the suction line and/or suction pump is divided across multiple locations on the suction device and not applied to the tissue via one port or hole, which would subject the tissue proximate to the port or hole to more trauma/damage from the force of the negative pressure.

In some embodiments, the suction device may include various materials, coatings, features, and/or components that make it visible to an imaging technique such as X-ray, Positron-emission tomography (PET), magnetic resonance imaging (MRI), computed tomography (CT), and the like. Additionally, or alternatively, the suction device may include an antimicrobial compound adapted to inhibit the growth of microbes and/or a leachable chemical such as a pharmaceutical intended to, for example, reduce swelling, reduce pain, and/or proximate to the suction device. In some instances, the suction device, suction device body, and/or extension may be adapted to be inserted easily into a patient via, for example, a smooth exterior surface and/or a coating (e.g., a lubricant) included thereon.

In some embodiments, the suction device may be adapted to inhibit interaction between and/or adhesion of tissue of a patient proximate to the suction device and the suction device. Exemplary interactions between the suction device and the tissue include movement, irritation, and inflation of the tissue. Inhibition of interaction and/or adhesion of tissue of a patient proximate to the suction device and the suction device may be achieved by, for example, a surface of the suction device that prevents adhesion/irritation of the tissue thereto and/or a coating (e.g., a lubricant) applied to the surface and/or embedded in the suction device that prevents irritation and/or adhesion of the tissue thereto. Additionally, or alternatively, spreading the force of the negative pressure provided to the first lumen via the second and third lumens across the plurality of holes of the suction device body acts to reduce the pressure applied to the tissue proximate the suction device body and, consequently, reduces the likelihood that the tissue will be sucked into, or otherwise perturbed by, the force of the negative pressure.

Some embodiments of the suction device include one or more support structures adapted to, for example, inhibit collapse of the suction device body and/or extension so that the respective first and/or second lumens may remain open upon the application of negative pressure thereto. For example, in one embodiment, the extension includes a center structural element that resides in the center of the second lumen thereby dividing the second lumen into a first-side extension (second) lumen and a second-side extension (second) lumen. The support structures may be flexible allowing the suction device body and/or extension to move when needed.

In some cases, the suction device(s) disclosed herein may be coupled to and/or invaginated into a suction line including a third lumen that is adapted for connection to the extension on a first end so that the third lumen is in communication with the second lumen and to a pump configured to apply a negative pressure to the third lumen on a second end. The suction line may be coupled to a tube as part of a medical device system. The tube may be flexible and hollow and allow gas to pass through. Exemplary medical device systems include a tracheal tube system, a laryngeal mask airway system, and a tracheostomy tube system.

In some embodiments, the medical device system may include an inflatable balloon and/or an inflatable cuff, as may be the case with, for example, a tracheal tube system, a laryngeal mask airway system, and a tracheostomy tube system. In these embodiments, the suction device body may be positioned proximate to the inflatable balloon and/or inflatable cuff so that, for example, negative pressure applied to the suction device may act to evacuate or otherwise remove fluid, secretions, and other matter from tissue of a patient proximate to the inflatable balloon and/or inflatable cuff. This may be effective in eliminating pools of secretions from areas of a patient's body proximate to the inflatable balloon and/or inflatable cuff which may, in turn, eliminate a breeding ground for microbes and reduce patient discomfort and tissue irritation associated with/caused by the pooling fluid.

BRIEF DESCRIPTION OF THE FIGURES

The present invention is illustrated by way of example, and not limitation, in the figures of the accompanying drawings, in which.

DETAILED DESCRIPTION

Figure 1:
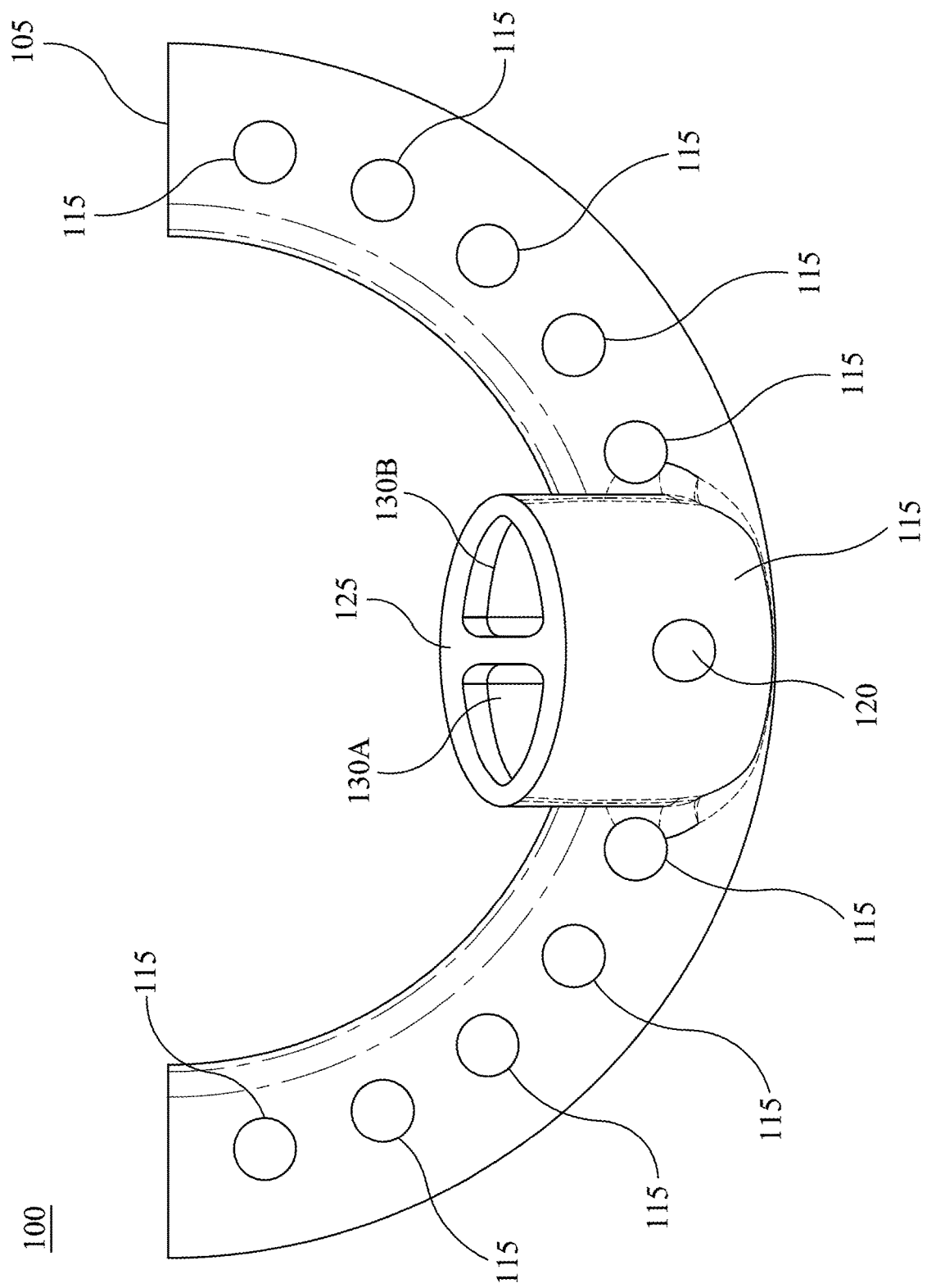
FIG. 1 provides a top plan view of an exemplary suction device, consistent with an embodiment of the present invention.

Disclosed herein are suction devices adapted for attachment to a suction line that may be provided by/associated with a tube (e.g., an tracheal tube) or other medical device (e.g., surgical tool, airway mask, etc.). The suction device may include a suction device body that includes, surrounds, and/or encases, a lumen. The suction device body, and/or one or more walls or surfaces thereof, may include one or more holes through which a solid, liquid, and/or gas may flow into the lumen from outside the suction device body. Often times the flow of the solid, liquid, and/or gas may be assisted by the application of negative pressure (or suction) by a source of negative pressure (e.g., a vacuum pump) that creates a negative pressure in the suction device via evacuation of air therefrom. The source of negative pressure/suction pump may be coupled to the suction device body via, for example, a suction line coupled to the suction pump and suction device body. The suction device may be configured to be coupled to a medical device, such as a tracheal tube system, an ablation tool system, a laryngeal mask airway system, and a tracheostomy tube system. On some occasions, the tube may have a lumen coupled to the suction device and negative pressure in the lumen may cause negative pressure in the suction device.

In some instances, the suction device may be curved or pre-configured into a particular shape (e.g., triangle, circle, etc.) and, in some instances, the suction device disclosed herein may be adapted for use with a variety of medical devices including, but not limited to, a tracheal tube, cutting device (e.g., scalpel or micro-scissors), ablation tool, laryngeal mask airway system, and/or tracheostomy system. The suction device may be affixed to the medical device via, for example, an ultrasonic-, chemical-, or heat-generated bond. Additionally, or alternatively, the suction device may be coupled to the medical device mechanically via, for example, a sleeve, a clip, a strap, and/or a clamp. In some instances, the medical device may include a hole or opening into which a portion of the suction device is inserted in order to facilitate attachment of the suction device to the medical device.

In many instances, the suction devices described herein will be shaped and positioned so as to be form-fitting and attached to a particular location of the medical device so that, for example, there are no gaps or depressions between the suction device and the medical device or a portion thereof. This is advantageous because, for example, when there are no regions between the suction device and the respective medical device where a liquid and/or solid may accumulate, complications (e.g., providing a collection pool and/or breeding ground for pathogens or irritants) caused by the accumulation of these fluids and/or solids may be avoided.

The form-fitting aspect of the various suction devices described herein may be achieved by configuring the suction devices to closely coincide with one or more exterior surfaces (or a portion thereof) of the medical device to which they are attached. For example, in a tracheal tube embodiment, a portion of the suction device may be curved with a first radius for a first type of tracheal tube or curved with a second radius for a second type of tracheal tube as may be the case with, for example, tracheal tubes of different sizes (e.g., adapted for use with an adult and a child).

Tracheal tube systems described herein may include a tube and a suction device. The tube may be flexible and hollow and have first and second open ends. The first end of the tube may be configured to be coupled to an artificial ventilation device and may be configured so as to allow air, or other gases provided by the artificial ventilation device, to flow through the tube into the lungs of an intubated (with the tracheal tube system) patient.

In many instances, the tracheal tube system also includes an inflatable balloon used to position, and maintain the position of, the tube in the trachea of an intubated patient. The inflatable balloon may be affixed to and circumferentially surround a portion of the tube at a position located between the first and second ends of the tube.

In some embodiments, the suction device may extend around a circumference, or a portion of a circumference, of the inflatable balloon and/or tube. In some cases, the suction device may be positioned proximate and/or adjacent to the inflatable balloon and/or a junction between the inflatable balloon and the tube but this need not always be the case. In some embodiments, the suction device may be positioned relative to the inflatable balloon such that when the tracheal tube system is inserted into a trachea, the balloon is inflated, and negative pressure is applied to the suction device by the suction device, the suction device is positioned against a portion of the tracheal wall, such as the posterior portion of the tracheal wall.

When the tracheal tube system is inserted in a patient's trachea, the negative pressure in the suction device may act to remove, or suction out, fluids and other matter from the trachea. In some cases, when the tracheal tube system is placed in a trachea, the negative pressure created by the suction device may act to hold the suction device against an inner surface or wall of the trachea thereby preventing movement of the secretions beyond the balloon and into the lower trachea or lungs of the patient.

The suction devices disclosed herein may be flexible, rigid, or some combination of both and may be made from any appropriate material including, but not limited to, silicon, plastic, vinyl, a bio-compatible material, and/or some combination thereof using any appropriate process including, but not limited to, injection molding or three-dimensional (3D) printing. In some circumstances, the suction device may be an assembly of two or more components. The suction devices, or portions thereof, disclosed herein may be flexible, rigid, or some combination of both. In some circumstances, the suction device may be an assembly of two or more components.

In some embodiments, one or more components of the devices and/or systems described herein may be coated with one or more materials/substances. Exemplary coating materials include medication or a pharmaceutical agent that may act to, for example, reduce swelling, reduce pain, and so on. Other exemplary coating materials include antimicrobial agents, lubricating agents, and agents that may prevent the adhesion of tissue of a patient and other matter to the suction device or other components of the tools/systems described herein.

In some embodiments, one or more components of a suction device disclosed herein may be made from a material that is, for example, slippery or known to have antimicrobial properties. Additionally, or alternatively, the suction devices disclosed herein may have an exterior surface designed to, for example, resist microbial growth and/or adhesion of a foreign substance (e.g., blood or phlegm) or tissue. In some circumstances, one or components of the devices and/or systems described herein may include/comprise a bio-absorbable material.

Turning now to the figures, FIGS. 1-9 illustrate an exemplary suction device 100 adapted to connect to and/or cooperate with a circular medical device such as a tracheal tube or ablation tool as viewed from several different perspectives. More specifically, FIG. 1 provides a top plan view of an exemplary suction device 100, which includes a suction device body 105, an extension 110, a plurality of holes or openings 115, a hole positioned in the extension 120, a center structural element 125, and a first-side lumen 130A, and a second-side lumen 130B.

Exemplary dimensions for suction device 100 components are as follows:
- Distance between ends of suction device body 105: 0.1-1.5 inches;
- Suction device body 105 exterior diameter: 0.05-0.3 inches;
- Suction device body 105 height (from the bottom of suction device body 105 to top of extension 110): 0.08-0.5 inches;
- Suction device body lumen 145 diameter: 0.04-0.2 inches;
- Thickness of material for suction device body 105 and/or extension 110: 0.015-0.035 inches;
- Hole 115 diameter: 0.01-0.1 inches; and
- Distance between holes 115: 0.03-0.1 inches.

Suction device body 105 may include a lumen 145 (shown in FIG. 4A) surrounded by the material used to fabricate suction device body 105. Lumen 145 may be of, for example, a circular, square, oval, or irregular cross section and may provide a pathway for the evacuation of liquids and other materials from, for example, tissue of a patient proximate to the suction device body 105 as may be the case with, for example, a trachea of an intubated patient or tissue surrounding an incision in a surgical field when negative pressure is applied to lumen 145. In this way, pools or other collections of secretions may be removed from the body on a continuous, periodic, and/or as-needed basis by being sucked into the openings or holes 115 and evacuated from the field via lumen 145 of suction device body 105. Often times, the negative pressure is applied to lumen 145 via a suction device coupled to a suction line coupled to suction device body 105 and/or extension 110 as described below with reference to FIGS. 10-17.

Extension 110 may extend orthogonally, or nearly orthogonally, from an exterior surface of suction device body 105 and may be centrally located relative to suction device body 105 so that negative pressure, or suction, applied to extension 110 is applied, in some cases, evenly applied, throughout lumen 145 of suction device body 105 thereby spreading out the area across which the force from the negative pressure is applied throughout the suction device 100. In some instances, extension 110 may be self-supporting (i.e., retain it's shape and position relative to suction device body 105 without the application of external force) and, in other instances, extension 110 may partially, or wholly, rely upon a medical device and/or suction line to which it is attached, such as the tracheal tube system discussed below with regard to FIGS. 10-12, for support.

As shown in FIG. 1, extension 110 includes a center structural element 125, although this need not be the case. Center structural element 125 may act to structurally support extension 110 and may separate a first-side lumen 130A of extension 110 from a second-side lumen 130B of extension 110. First-side and second-side lumens 130A and 130B may be open to lumen 145 so that solids, liquids, and/or gases flowing through lumen 145 may also flow through first-side and/or second-side lumens 130A and 130B and up through a lumen of a suction line coupled to extension 110.

Center structural element 125 may also assist with preventing occlusions to suction device body 105, lumen 145, first-side lumen 130A, and/or second-side lumen 130B, or a portion thereof. For example, if a solid, or semi-solid object (e.g., a mucus plug) is sucked up one of the holes 115 positioned on a first side of suction device body 105, only the first-side lumen 130A (i.e., the lumen 130 corresponding to the side of the suction device body 105 that includes the hole that sucked up the solid, or semi-solid object is located) may be occluded by the solid/semi-solid object because center structural element 125 isolates the occluded first-side lumen 130A from the open second-side lumen 130B. In this way, suction device 100 may function and serve one or more of its intended purposes while being partially occluded.

Figure 2:
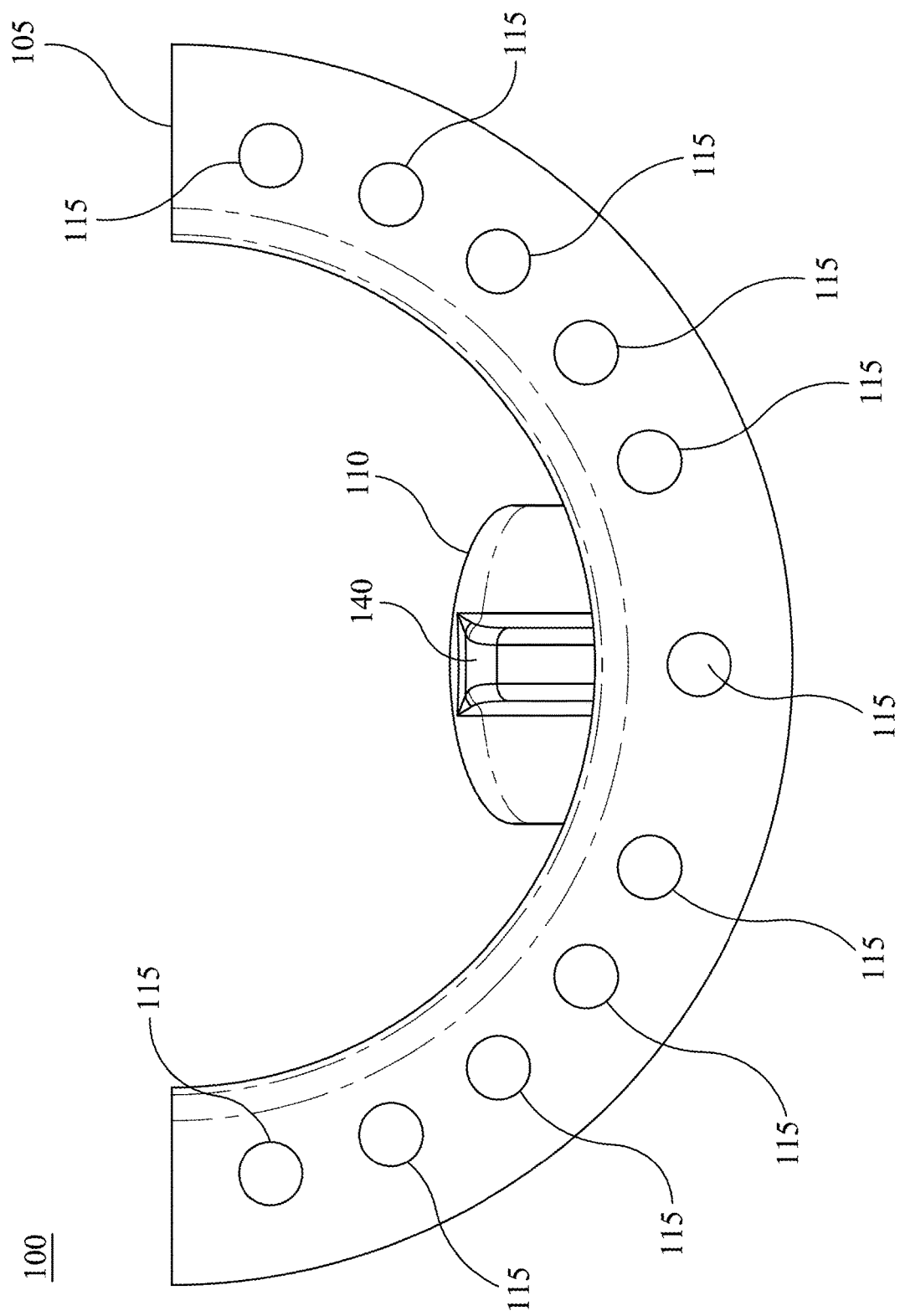
FIG. 2 depicts a bottom plan view of the exemplary suction device, consistent with an embodiment of the present invention.

FIG. 2 depicts a bottom plan view of exemplary suction device 100 and shows the underside of suction device body 105 and extension 110. Bottom plan view of suction device 100 also shows a plurality of holes 115 through a bottom portion of a wall or material making up suction device body 105. In some instances, one or more of the plurality of holes 115 on a lower portion of the wall may align with one or more of the holes 115 on the upper portion of the wall. FIG. 2 also depicts a structural element 140 of extension 110. Structural element 140 may serve to support the extended, or upright, state of extension 110 and/or facilitate attachment of suction device 100 to a suction line and/or medical device (e.g., tracheal tube system) as will be discussed in greater detail below with regard to FIGS. 10-12.

In most instances, an entire suction device 100 may be made from one material however, this need not be the case. For example, in one embodiment, suction device body 105 may be made from one material (e.g., silicon) and extension 110 may be made from a different material (e.g., plastic). In one embodiment of this example, the suction device body 105 may be made from a flexible material like silicon and extension 110 may be made from a material with more rigidity than silicon like plastic. In some instances, suction device body 105 and/or extension 110 may include a rigid, or semi-rigid structure or skeleton that is coated, or otherwise covered, with a soft, smooth, and/or flexible material.

Figure 3:
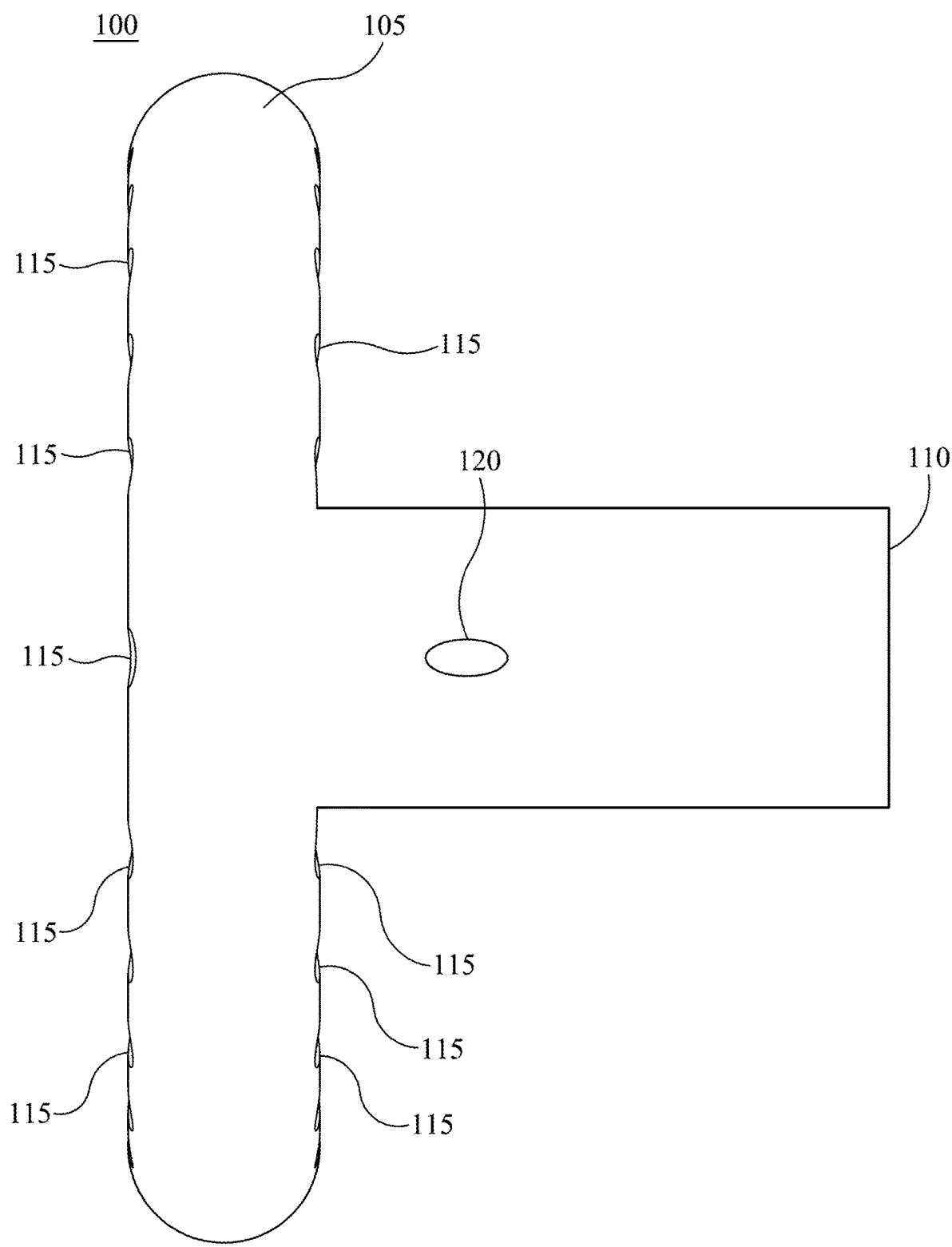
FIG. 3 provides a front view of the exemplary suction device, consistent with an embodiment of the present invention.
Figure 4A:
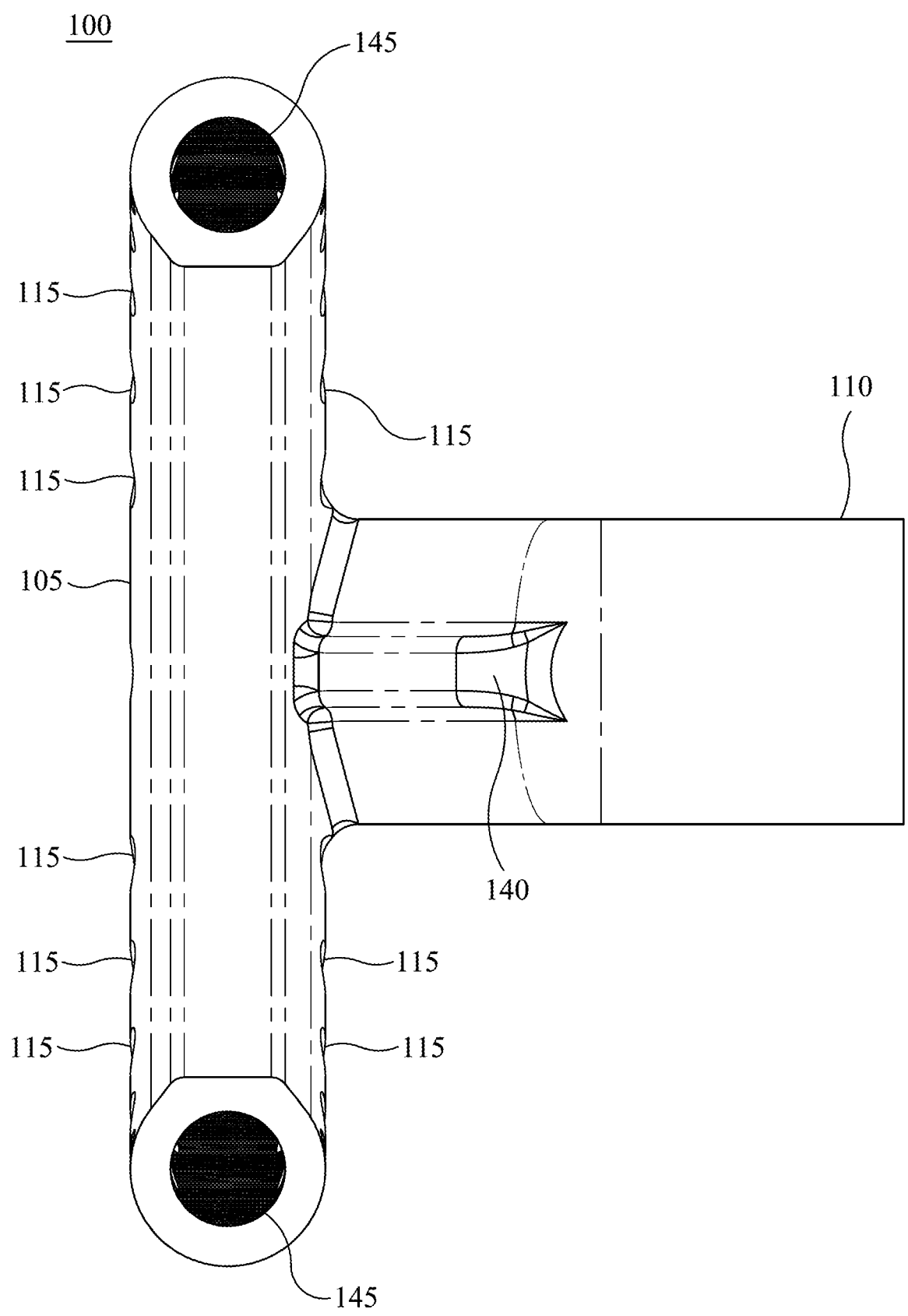
FIG. 4A depicts a back view of the exemplary suction device with open ends for suction device body, consistent with an embodiment of the present invention.
Figure 4B:
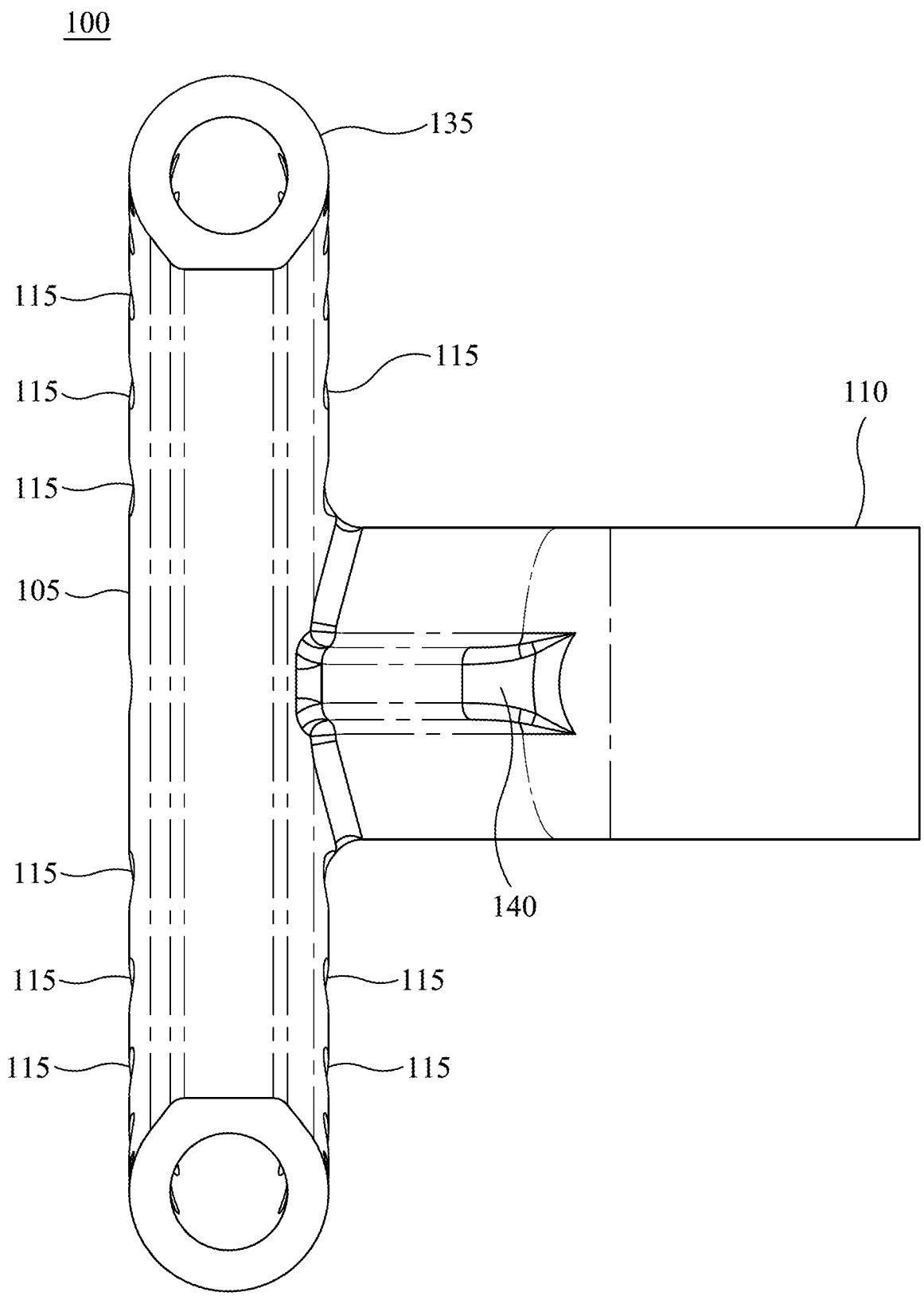
FIG. 4B depicts a back view of the exemplary suction device with closed ends for suction device body, consistent with an embodiment of the present invention.

FIG. 3 provides a front view of exemplary suction device 100, FIG. 4A depicts a back view of exemplary suction device 100 with open ends for suction device body 105 so that lumen 145 of suction device body 105 may be seen. FIG. 4B depicts a back view of exemplary suction device 100 with closed ends, or end caps 135, which serve to seal off, or close lumen 145. End caps 135 may be formed by, for example, affixing (via, for example, a chemical or heat-sealed bond) the top and bottom of suction device body 105 together or by affixing an end cap 135 to the suction device body 105. In another embodiment, end cap 135 may be a seamless extension of the material used to form suction device body 105 as may be produced by, for example, injection molding.

In addition, as can be seen in FIGS. 4A and 4B, structural element 140 extends from a junction between suction device body 105 and extension 110 to a position partially up extension 110. In some instances, end caps 135 may include a hole or other opening by which, for example, fluids and other materials may be sucked from the trachea of a patient.

Figure 5:
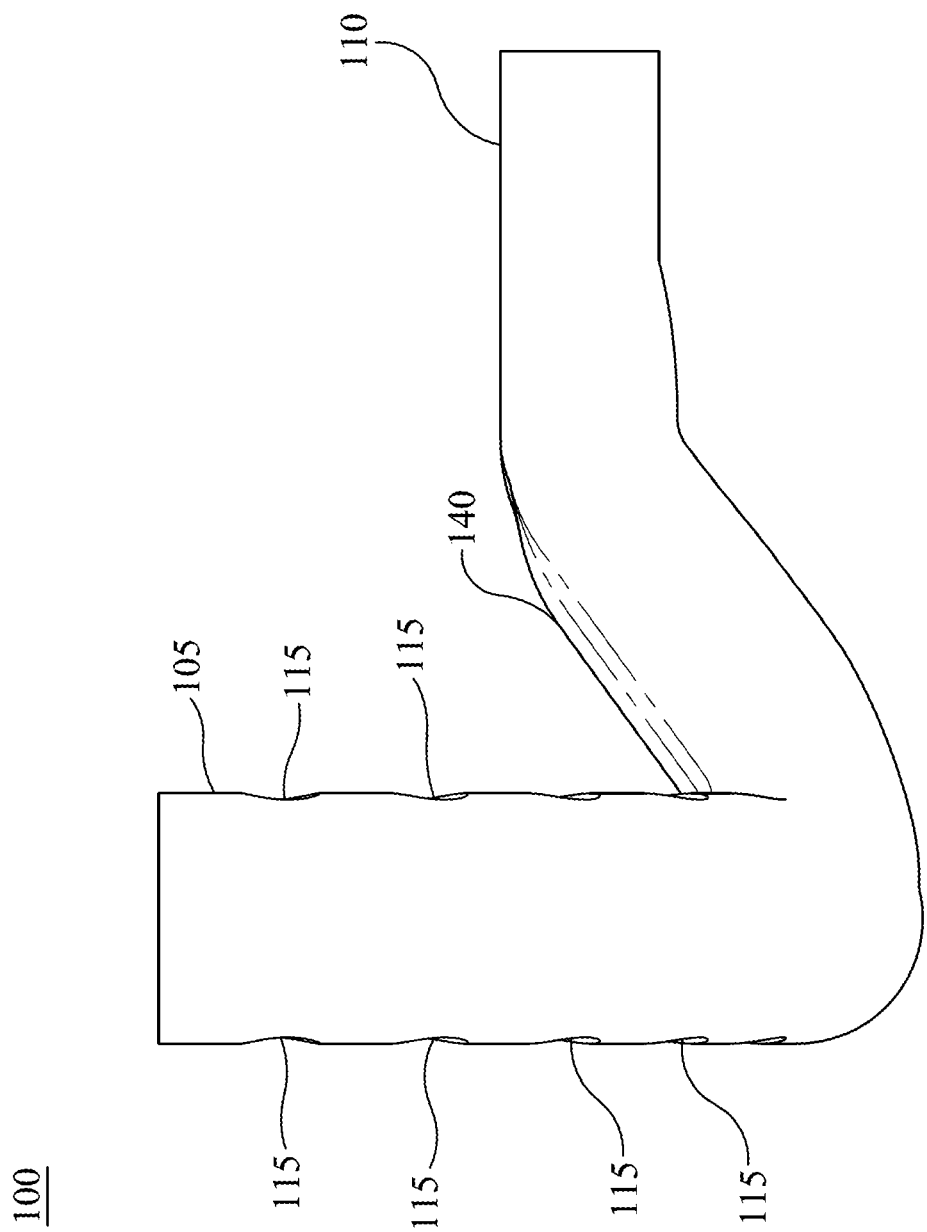
FIG. 5 depicts a side view of the exemplary suction device, consistent with an embodiment of the present invention.
Figure 6:
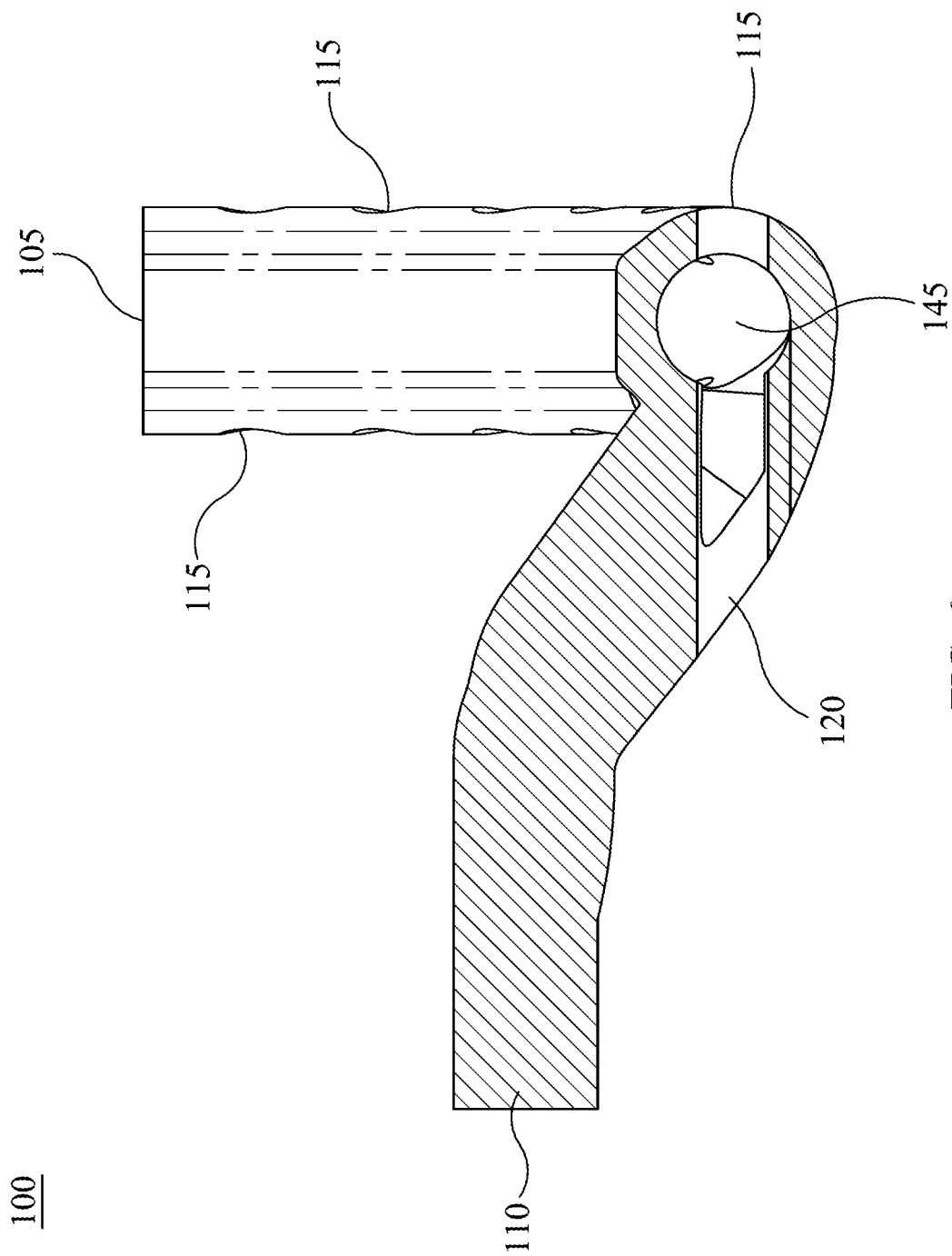
FIG. 6 offers a cross-section view of the exemplary suction device, consistent with an embodiment of the present invention.

FIG. 5 depicts a side view of exemplary suction device 100 and FIG. 6 depicts a cross-section view of suction device 100. FIG. 6 offers a cross-section view of exemplary suction device 100 wherein an interior surface of extension 110 is shown with patterned shading. FIG. 6 shows how holes 115 and 120 extend through suction device body into lumen 145. The view of FIG. 6 does not show center structural element 125.

Figure 7:
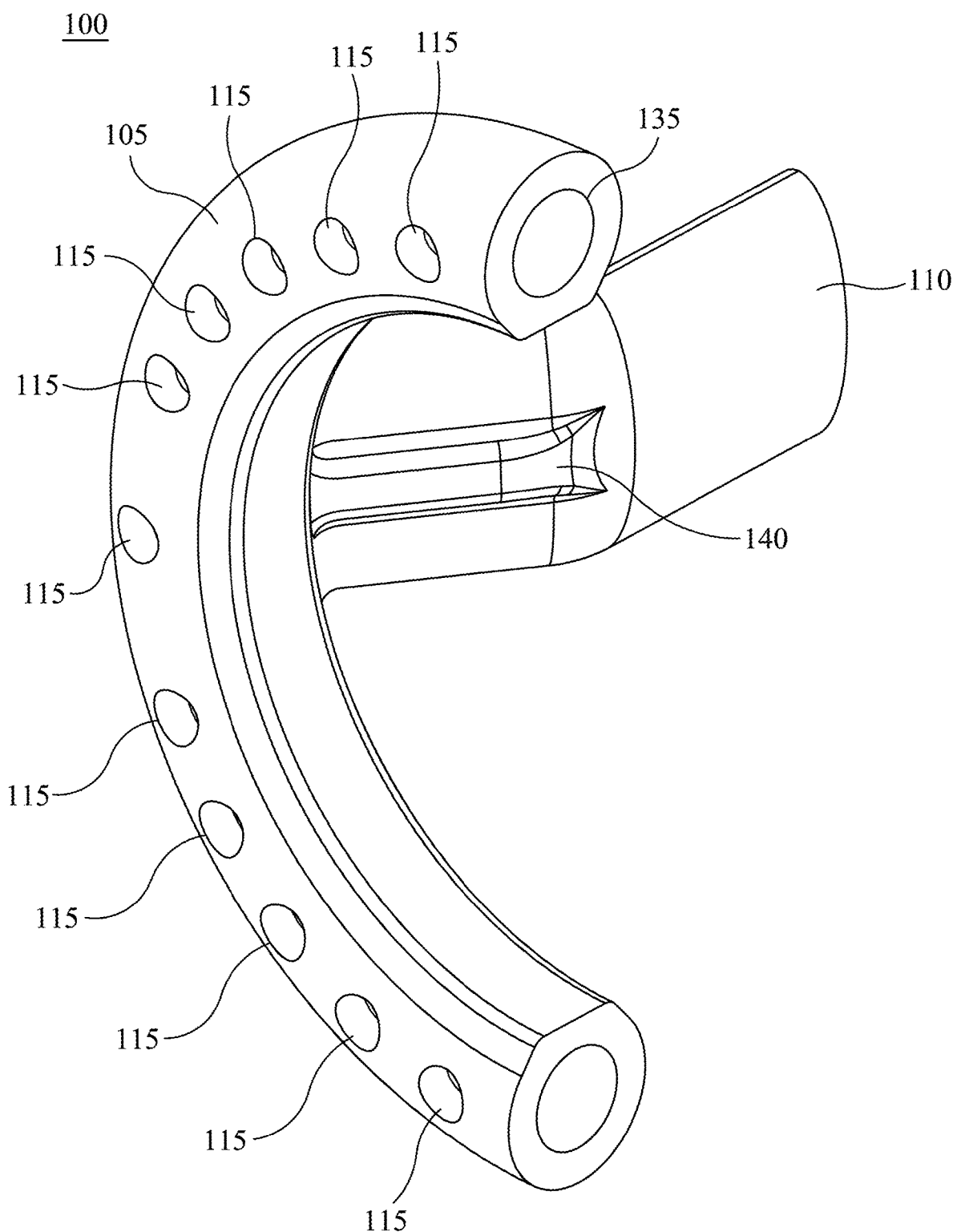
FIG. 7 provides a bottom-rear perspective view of the exemplary suction device, consistent with an embodiment of the present invention.
Figure 8:
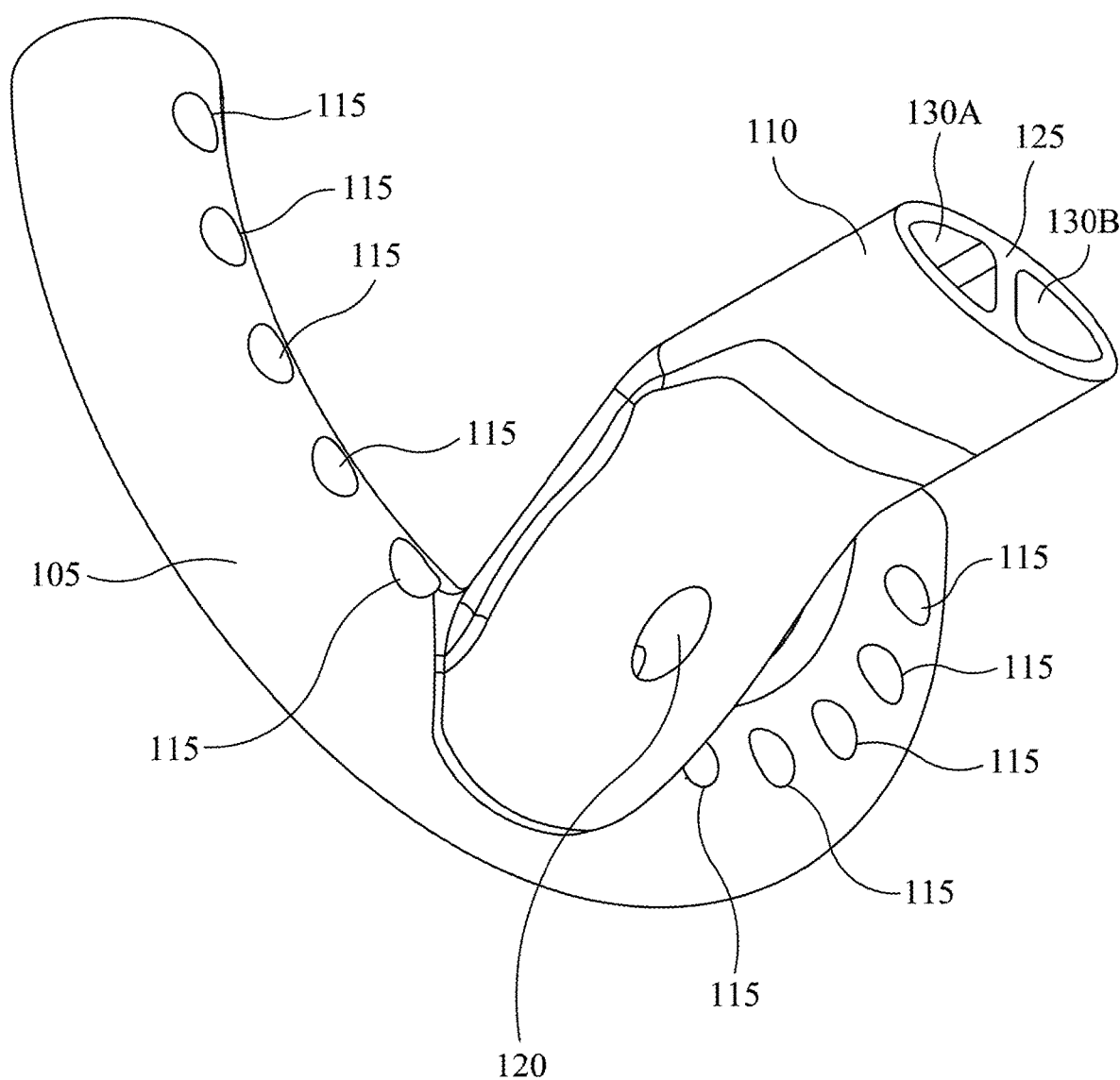
FIG. 8 provides a top-front perspective view of the exemplary suction device, consistent with an embodiment of the present invention.
Figure 9:
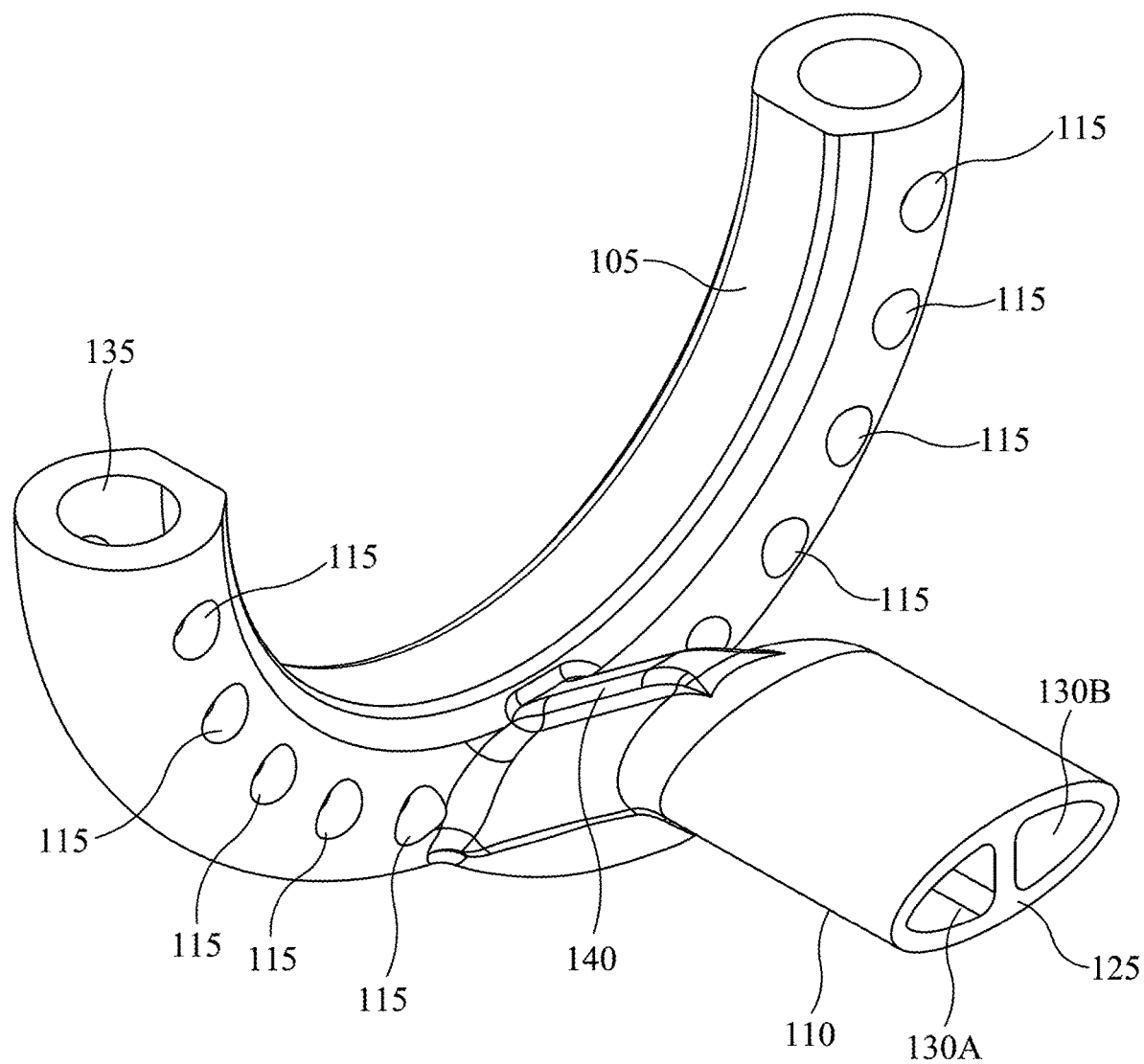
FIG. 9 provides a front-top perspective view of the exemplary suction device, consistent with an embodiment of the present invention.

FIGS. 7-9 provide various perspective views of an exemplary suction device 100. More specifically, FIG. 7 provides a bottom-rear perspective view of the exemplary suction device 100, FIG. 8 provides a top-front perspective view of the exemplary suction device 100, and FIG. 9 provides a front-top perspective view of the exemplary suction device 100.

Figure 10:
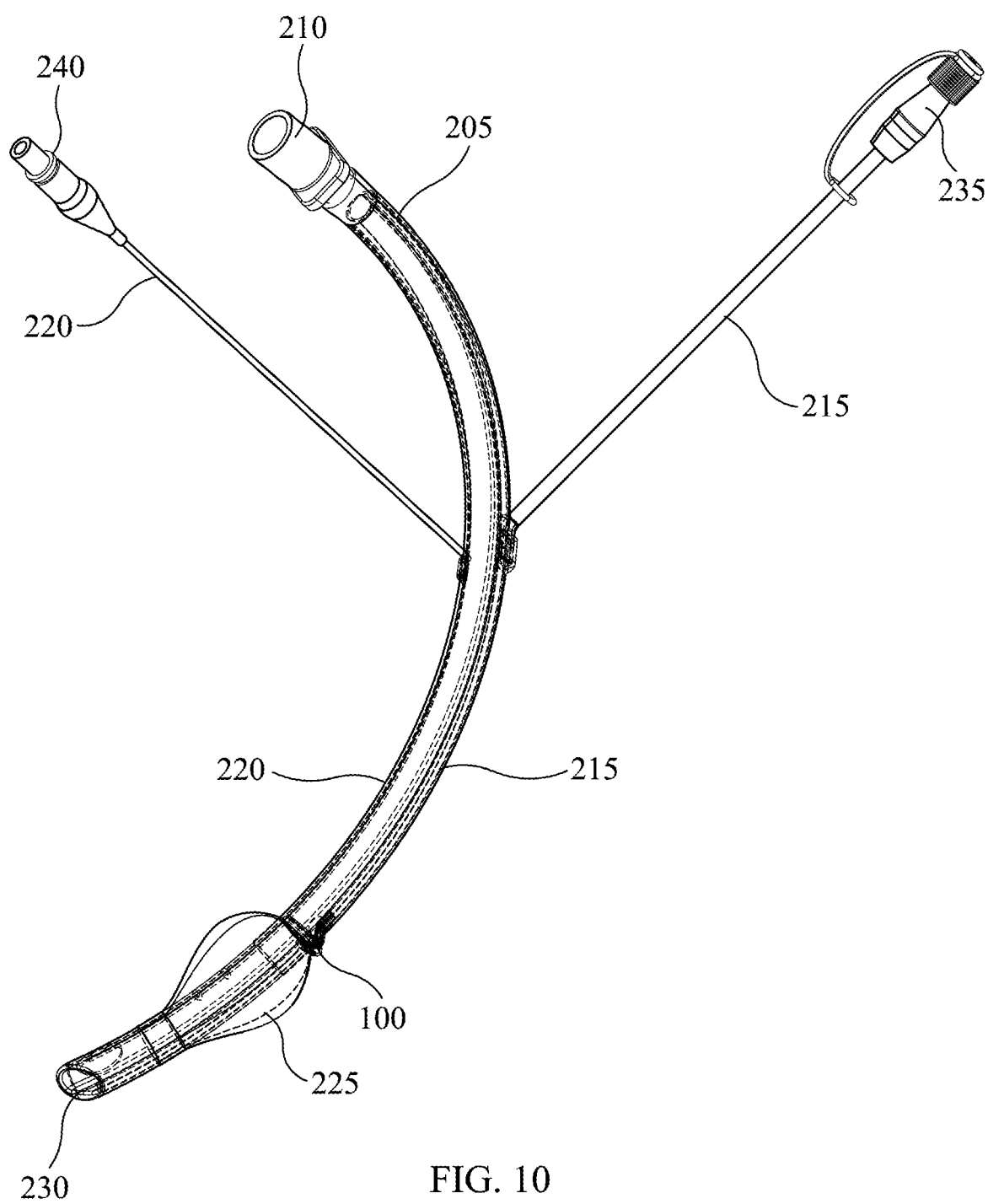
FIG. 10 provides a view of an entire exemplary tracheal tube system, consistent with an embodiment of the present invention.
Figure 11:
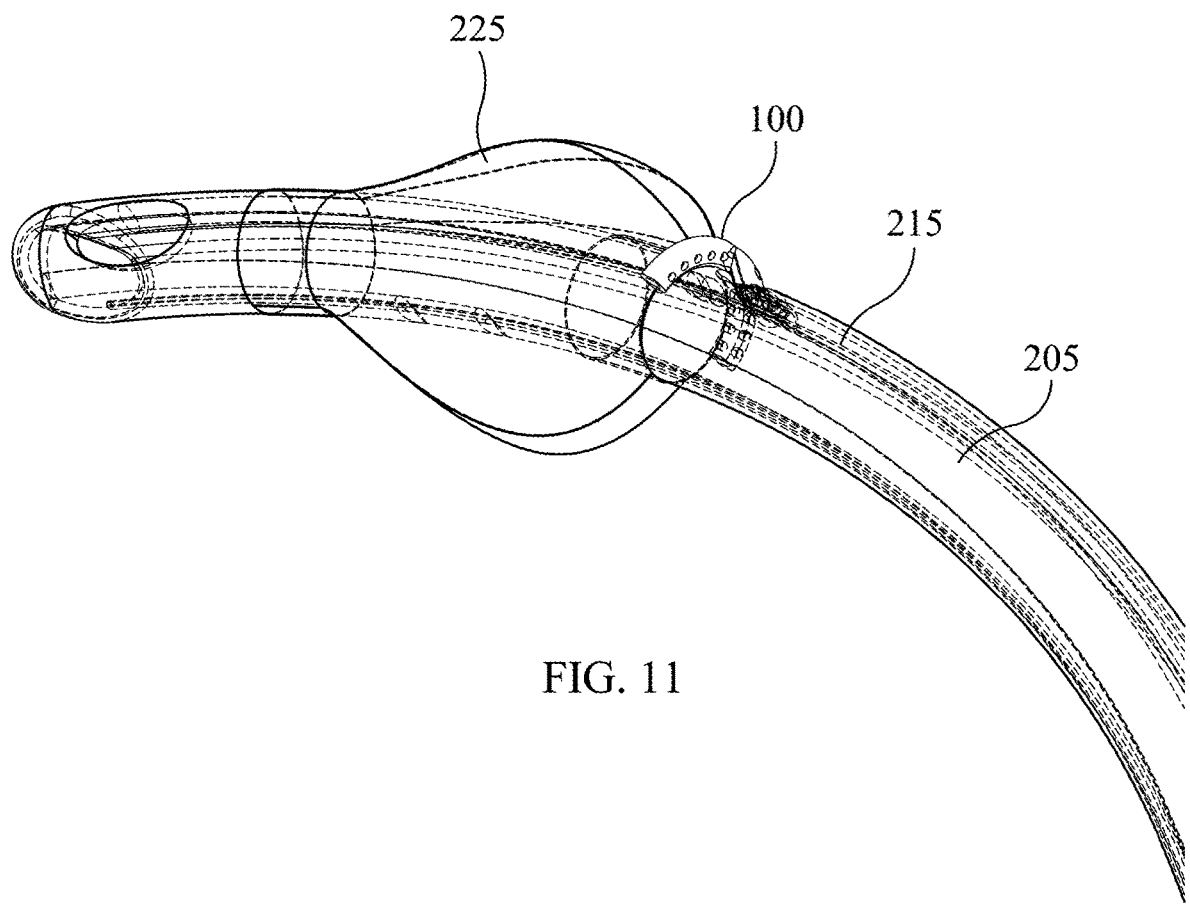
FIG. 11 provides a close-up rear perspective view of a portion of the exemplary tracheal tube system that includes the exemplary suction device, consistent with an embodiment of the present invention.
Figure 12:
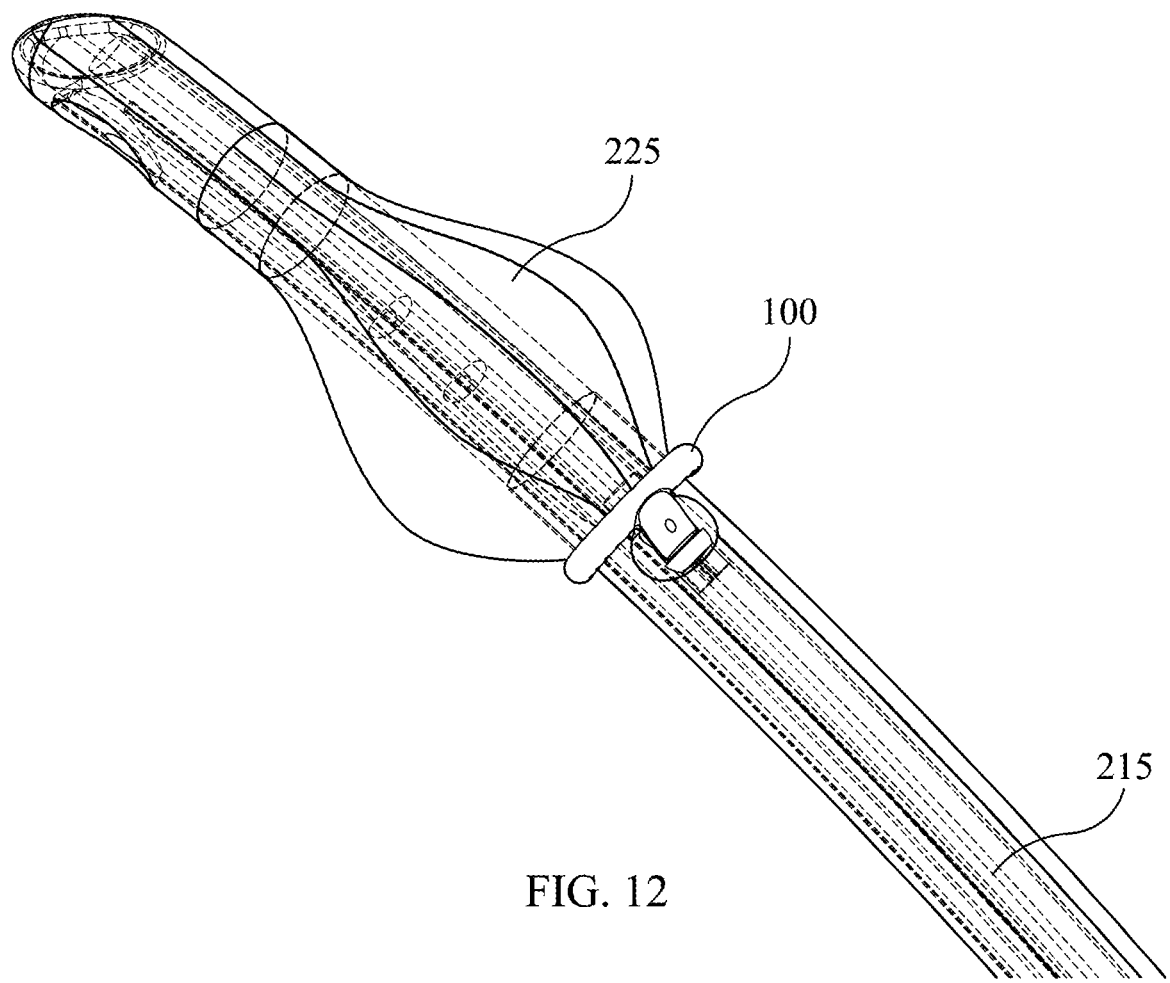
FIG. 12 provides a close-up front perspective view of the portion of the exemplary tracheal tube system that includes the exemplary suction device, consistent with an embodiment of the present invention.

FIGS. 10-12 provide illustrations of an exemplary suction device 100 when incorporated into a medical device in the form of an exemplary tracheal tube system 101 with FIG. 10 providing a view of the entire exemplary tracheal tube system 101, FIG. 11 providing a close-up rear perspective view of the portion of exemplary tracheal tube system 101 that includes suction device 100, and FIG. 12 providing a close-up front perspective view of the portion of exemplary tracheal tube system 101 that includes suction device 100. Tracheal tube system 101 includes an exemplary suction device 100, a tube 205 with a first end 210 and a second end 230. Tracheal tube system 101 may also include a suction line 215 that extends down a portion of tube 205, a suction line adapter 235, an inflatable balloon 225, an inflation line 220, and an inflation line adapter 240.

Tube 205 may be configured so as to allow air or other gases provided by an artificial ventilation device (coupled to first end 210) to flow through the first tube into the lungs of an intubated (with tracheal tube system 101) patient. The second end 230 of tube 205 may be configured to pass air or other gasses into the lungs of the intubated patient.

Tube 205 may include an inflatable balloon 225 positioned between the first end 210 and second end 230 of tube 205 and may circumferentially surround a portion of tube 205. Inflatable balloon 225 may remain un-inflated, or deflated, until tracheal tube system 101 is inserted into a patient's trachea and positioned appropriately therein. Once tracheal tube system 101 is properly positioned within the patient's trachea, inflatable balloon 225 may be inflated using air, or another gas, passed through inflation line 220 from an inflation pump (not shown) attached to inflation line adapter 240. Inflating inflatable balloon 225 to a desired degree of inflation while positioned within the patient's trachea may serve to stabilize tracheal tube system's 101 positioning within the patient's trachea/throat and may also serve to prevent an unintentional, or undesired, gas and/or liquid exchange between the patient's lungs and the patient's trachea and/or outside environment.

Suction device 100 may be positioned within/on tracheal tube system 101 at, or proximate to, a junction between inflatable balloon 225 and tube 205. Suction device 100 may be affixed, or otherwise connected, to tracheal tube system 101 via, for example, mechanical means using, for example, a clip, screw-like adapter, or other mechanical joining device (e.g., tab, insertion of extension 110 into suction line lumen). In some embodiments, suction device 100 may be permanently affixed to tube 205 but this need not be the case. For example, suction devices 100 of different sizes or shapes may be interchangeably connected/affixed to tube 205.

In the embodiment of FIGS. 10-12, suction device 100 is permanently affixed to tube 205 and/or suction line 215 via insertion of extension 110 into an opening, or hole, (not shown) within tube 205 and/or suction line 215 and then permanently bonding extension 110 to tube 205 and/or suction line 215 via, for example, a chemical, ultrasonic, or thermal bonding process to tube 205. Once inserted into this hole, extension 110 forms a seal (in most cases, an air-tight seal) with suction line 215 and/or a suction line lumen included therein (not shown) and suction, or negative pressure, supplied by suction line lumen 215 will be applied to extension 110 and suction device body 105 via lumens 130A, 1308, and 145. In some instances, a bonding process between extension 110 and suction line lumen may facilitate the seal between extension 110 and suction line 215 and/or a lumen included therein. In some circumstances, suction device 100 is invaginated into one or more components of tracheal tube system 101 (e.g., suction line 215 and/or tube 205).

Suction device 100 is affixed to tube 205 and/or suction line 215 in such a way as to substantially maintain the shape and configuration of extension 110 as well as center structure 125, first-side lumen 130A and second-side lumen 130B. In this way, lumen 145 as well as first-side lumen 130A and/or second-side lumen 1308 remain open and free from occlusion so that gases, fluids, and/or other substances may be sucked (e.g., from an area of the a patient's trachea proximate to the suction device 100) through the plurality of holes 115 via application of negative pressure (i.e., suction) applied to suction tube 215 by a suction pump attached to suction line 215 via suction line adapter 235. In this way, the fluids and/or other substances may be evacuated from the patient's trachea thereby reducing and, in some instances, eliminating a leaking of a volume of fluids and/or other substances past the inflatable balloon 225 and into the lungs of the patient. In this way, pools or other collections of secretions may be removed from the body on a continuous, periodic, and/or as-needed basis by being sucked into the openings or holes 115 and evacuated from the field via the lumens 145, 130A and/or 1308.

In some instances, suction device 100 may touch and/or be affixed to inflatable balloon 225 and, in other instances; inflatable balloon 225 may be independent (i.e., not attached to and/or touching) inflatable balloon 225. On some occasions, suction device 100 may reside within an indentation (not shown) positioned on an exterior surface of inflatable balloon 225 and/or an indentation positioned on an exterior surface of tube 205.

Figure 13:
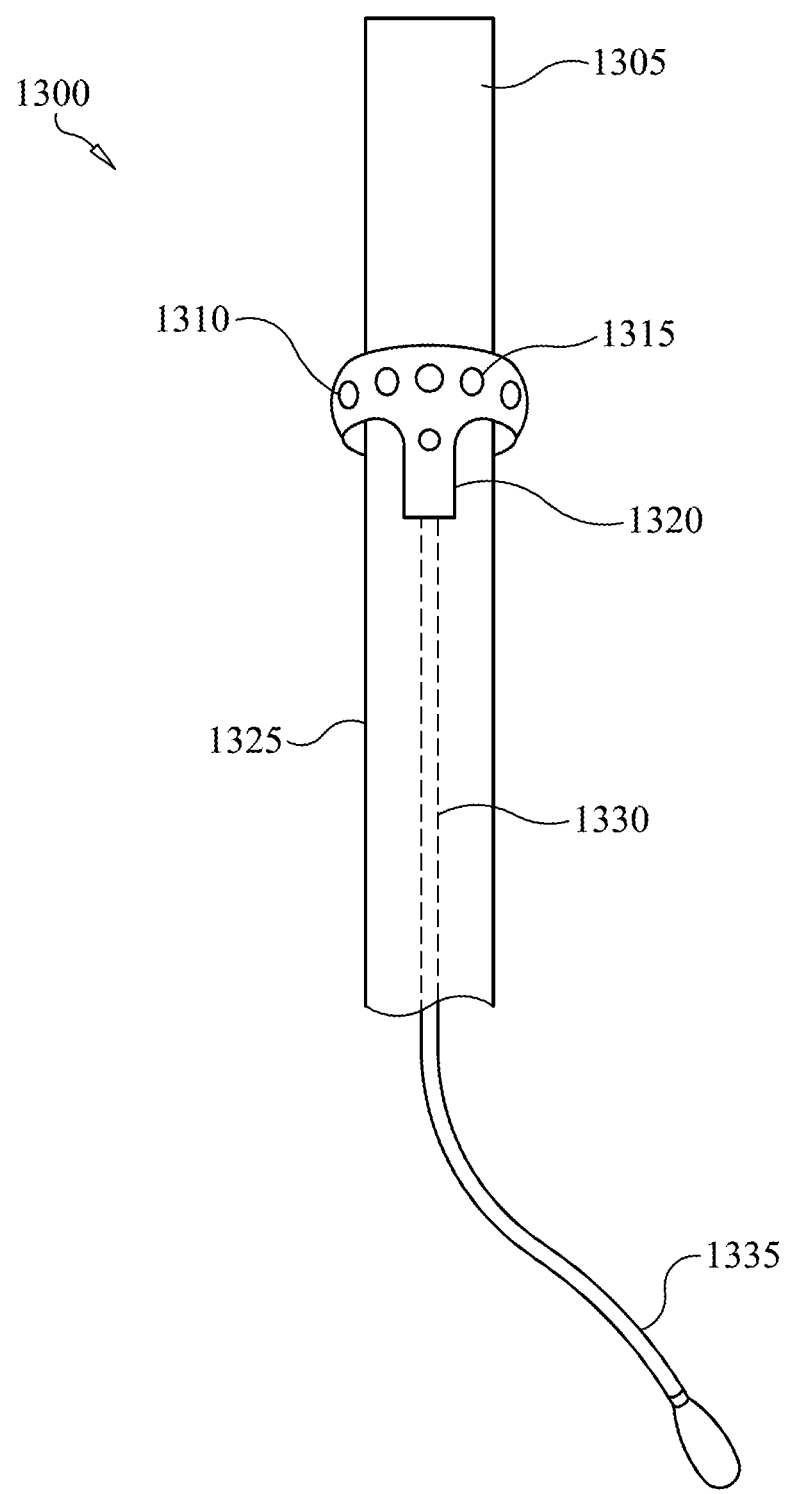
FIG. 13 shows an exemplary ablation tool system, consistent with an embodiment of the present invention.

FIG. 13 shows an exemplary ablation tool system 1300 that includes an ablation tip 1305, a suction device 1310, and a handle 1325. The suction device 1310, which may have one or more features in common with the suction devices discussed herein, includes one or more openings or holes 1315 and a suction line extension 1320 adapted to couple to a suction line 1330 resident within and/or coupled to handle 1325. Suction line 1330 may run the length of handle 1325 and may be coupled to an adapter 1335 configured to couple to a source of negative pressure (not shown), such as a vacuum pump (not shown).

Suction device 1310 may be any size and shape appropriate for ablation tool system 1300, ablation tip 1305, and/or handle 1325. Exemplary shapes for suction device 1310 are circular, semi-circular, linear, and/or rectangular. In some instances, suction device 1310 may wrap completely (i.e. 360°), or partially (e.g., 90°, 180°, or 270°), around a base of ablation tip 1305. Additionally, or alternatively, suction device 1310 may wrap around ablation tip 1305 and/or handle 1325 more than once in, for example, a spiral or circular fashion. Also, it should be noted that while only one suction device 1310 is shown in FIG. 13, this need not be the case. For example, ablation tool system 1300 may employ two or more suction devices 1310.

Suction device 1310 and/or suction line extension 1320 may be made from a flexible (e.g., silicon) material and/or a rigid (e.g., plastic) material. In some instances, suction line extension 1320 may be made from the same material as suction device 1310 and, in other instances, it may be made from a different material. Suction line extension 1320 may attach to suction line 1330 via, for example, a mechanical, chemical, and/or thermo bonding method. In most instances, suction device 1310 will include a lumen (not shown) that gas, liquids, and/or solids may pass through upon, for example, the application of negative pressure from a negative pressure source (e.g., a vacuum pump) coupled to suction line 1330 via adapter 1335. The gas, liquids, and/or solids may enter the lumen of suction device 1310 by way of one or more of the holes 1315.

When ablation tool system 1300 is used in a surgical field, ablation tip 1305 may ablate, or burn, tissue or bodily fluids and suction device 1310 may act to evacuate, for example, smoke, bodily fluids, tissue, and so on from the surgical field that may result from the ablations and/or other facets of a surgery (e.g., cutting, clamping, etc.). Suction device 1310 may evacuate the smoke, bodily fluids, tissue, etc. by the application of negative pressure to the surgical field via openings or holes 1315 using suction line 1330 and suction line adaptor 1335. In this way, smoke, bodily fluids, tissue, etc. may be evacuated away from the surgical field by being sucked into the openings or holes 1315 and evacuated from the field via the lumen of suction line 1330 while surgery is being performed. This may lead to better surgical outcomes because a surgeon is better able to see in the surgical field (due to reduced smoke, fluids, etc.) and does not need to introduce a separate suction device (e.g., cannula) into the surgical field, thereby reducing the trauma to surgical field caused by insertion and removal of the separate suction device.

Figure 14:
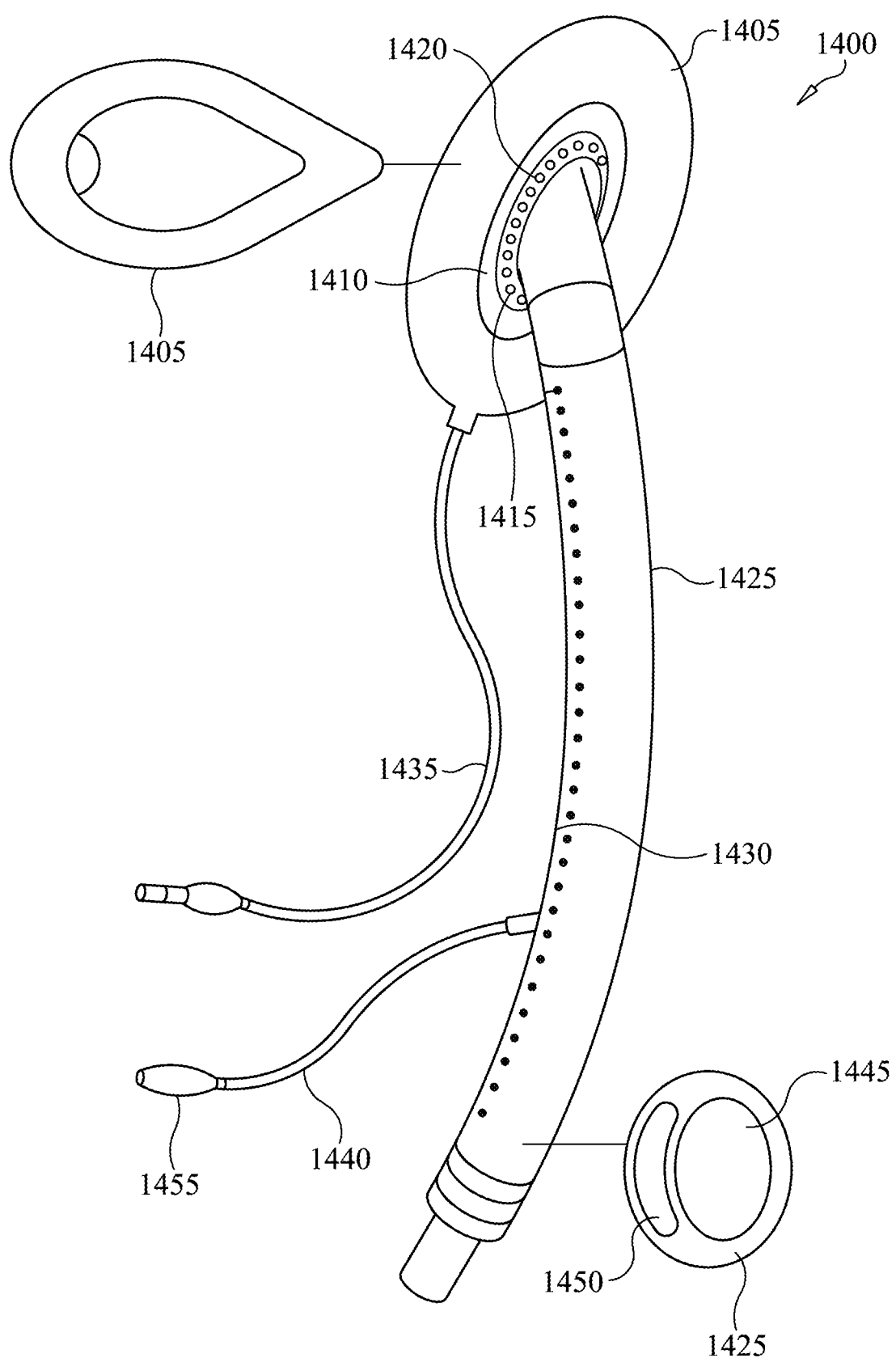
FIG. 14 shows a first exemplary laryngeal mask airway system, consistent with an embodiment of the present invention.
Figure 15:
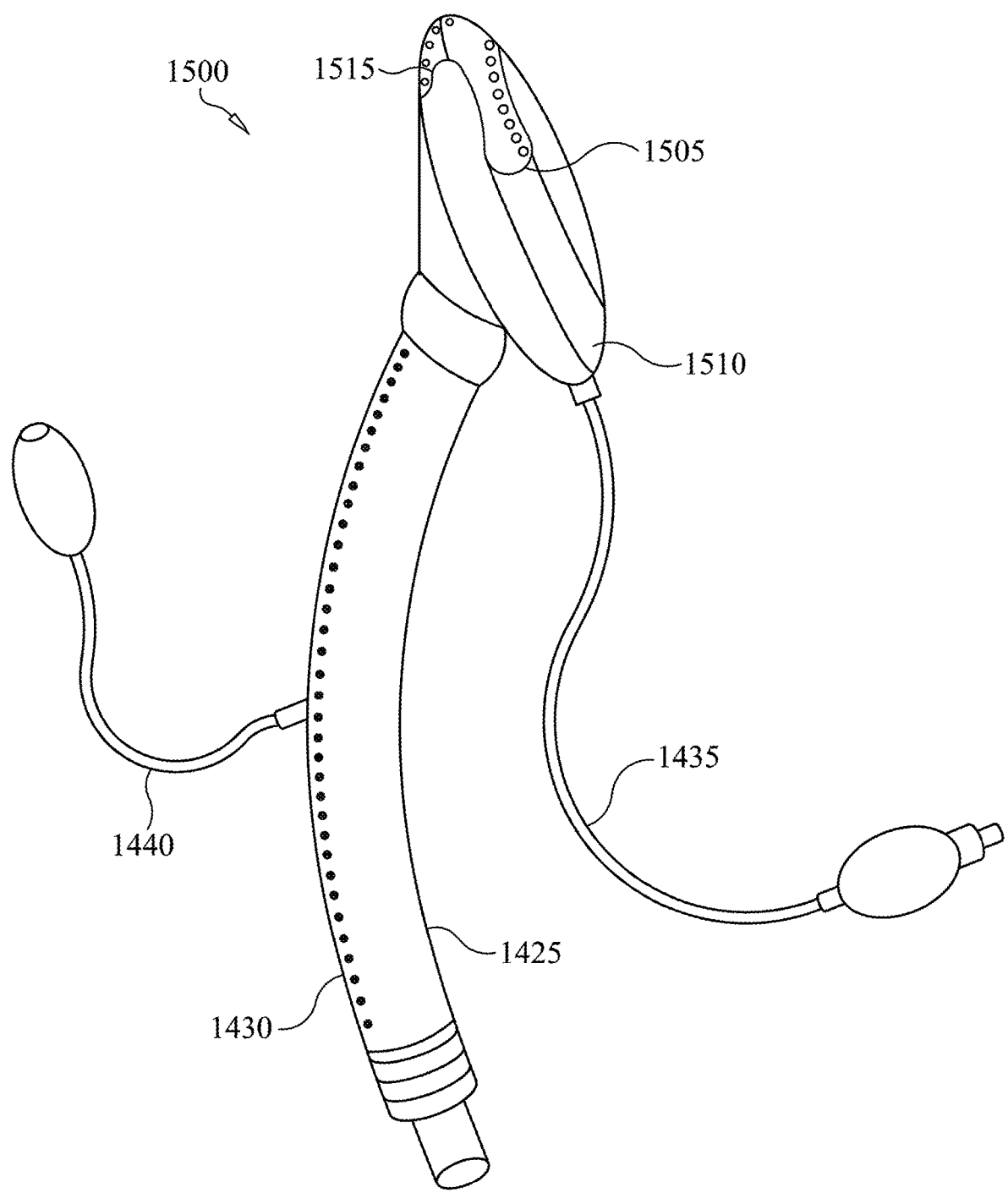
FIG. 15 shows a second exemplary laryngeal mask airway system, consistent with an embodiment of the present invention.

FIGS. 14 and 15 show a first and second exemplary laryngeal mask airway system 1400 and 1500, respectively. More specifically, FIG. 14 provides a side perspective view of first laryngeal mask airway system 1400, a bottom plan view of an inflatable cuff 1405 thereof, and a cross section of a tube 1425 thereof. First laryngeal mask airway system 1400 includes inflatable cuff 1405, a cuff depression 1410, a suction device 1415, tube 1425, a suction line 1430, an inflation line 1435, an external suction line 1440, and an adapter 1455. As shown in the cross section view of tube 1425, tube 1425 may include a tube lumen 1445, and a suction line lumen 1450.

Suction device 1415, which may have one or more features in common with the suction devices discussed above, may be adapted to couple to (e.g., be inserted into) suction line 1430, which may be resident within and/or coupled to tube 1425. Suction line 1430 may run the length of tube 1425 or may run the length of the tube until it is coupled to and/or extends to form external suction line 1440. Adapter 1455 of suction line 1440 may be configured to couple to a source of negative pressure (not shown), such as a vacuum pump so that negative pressure may be applied to external suction line 1440, suction line 1430, and suction device 1415 so that, for example, fluids, solids, and/or gasses may be sucked into a lumen present in suction device 1415 via one or more openings or holes 1420 positioned on/through an exterior surface of suction device 1415 in a manner similar to that described above with regard to suction device(s) 100 and 1300.

As may be seen in the bottom plan view of cuff 1405 provided by FIG. 14, cuff 1405 has a substantially elliptical or tear-drop-like shape and is designed to be inserted into a patient's mouth, down his or her windpipe, and deployed (i.e., inflated) so as to form an airtight seal above the glottis. Suction device 1415 may be any size and shape appropriate for laryngeal mask airway system 1400, cuff 1405, and/or cuff depression 1410. As shown in FIG. 14, cuff depression 1410 occurs where the cuff 1405 is joined to tube 1425 and suction device 1415 may partially, or wholly, rest within, and/or be bonded to, cuff depression 1410. In some embodiments, suction device 1415 is embodied as a tube that extends from a junction with suction line 1430 around the entirety of the cuff depression 1410 and back to the junction with suction line 1430. In some instances of this embodiment, a first end of suction device 1415 may be open and coupled to suction line 1430 and a second end may be sealed and, for example, attached to cuff 1405 and/or tube 1425. In this instance, suction device 1415 may only have one open end by which to apply negative pressure to holes 1420. In other instances of this embodiment, suction device 1415 may have two open ends, either, or both of which may couple to suction line 1430. Suction device 1415 may attach to suction line 1430 via, for example, a mechanical, chemical, and/or thermo bonding method. In some embodiments, suction device 1415 may only partially wrap around and/or cover cuff depression 1410.

Suction device 1415 may be made from a flexible (e.g., silicon) material and/or a rigid material (e.g., plastic) and, in many cases, may have a tube-like shape with a lumen, like lumen 145 in the center. Suction line lumen 1450 may be accessed via the plurality of holes or openings 1420. Gas, liquids, and/or solids may pass through holes 1420 upon, for example, the application of negative pressure from a negative pressure source (e.g., a vacuum pump) coupled to external suction line 1440 via adapter 1455 and indirectly coupled to suction line 1430. In many instances, liquids, such as saliva and other bodily secretions will be evacuated from a patient's airway via use of suction device 1415 and/or laryngeal mask airway system 1400.

Suction device 1415 may be positioned relative to inflatable cuff 1405 so as to be located in a region where secretions are likely to gather due to, for example, gravitational forces and/or patient anatomy. Suction device 1415 may also be positioned so as to evacuate gastric, or other, secretions that may otherwise spread to the lungs of a patient.

Turning now to FIG. 15, laryngeal mask airway system 1500 includes a cuff 1510, a suction device 1505, a tube 1425, a suction line 1430, an inflation line 1435, and an external suction line 1440. Suction device 1505, which may have one or more features in common with the suction devices discussed above, includes one or more openings or holes 1515 by which liquids, solids, or gasses may be evacuated from a patient via the application of negative pressure to external suction line 1440, suction line 1430, and suction device 1505. Suction line 1430 may run the length of tube 1425 and may joined to eternal suction line 1440 that includes an adapter configured to couple to a source of negative pressure (not shown), such as a vacuum pump. Alternatively, suction line 1430 may terminate at and/or extend to form external suction line 1440.

Suction device 1505 may be any size and shape appropriate for laryngeal mask airway system 1500 and/or cuff 1510. In some instances, suction device 1505 may be an integral part of cuff 1510. As shown in FIG. 15, suction device 1505 is coincident with and/or affixed to a portion of cuff 1510 designed to first enter a patient's mouth or airway. In some embodiments, suction device 1505 may extend from an exterior surface of cuff 1510 and, in other embodiments, an outer surface of suction device 1505 may be coincident (i.e., flush) with an external surface of cuff 1510. In the embodiment of FIG. 15, suction device 1505 covers a portion of an exterior surface of cuff 1510 so as to, for example, evacuate secretions from a patient's airway when in use. In some embodiments, suction device 1505 is embodied as a tube that extends from a junction with suction line 1430 around a portion of the cuff 1510.

Suction device 1505 may be made from a flexible (e.g., silicon) material and/or a rigid material (e.g., plastic) and, in many cases, may have a lumen (not shown) in the center that is like lumen 145. This lumen may be accessed via the plurality of holes or openings 1510. Gas, liquids, and/or solids may pass through holes 1510 upon, for example, the application of negative pressure from a negative pressure source (e.g., a vacuum pump) coupled to suction line 1430 via adapter 1440. In many instances, liquids, such as saliva and other bodily secretions will be evacuated from a patient's airway via use of suction device 1505.

Suction device 1505 may be positioned relative to cuff 1510 so as to be located in a region where secretions are likely to gather due to, for example, gravitational forces and/or patient anatomy. Suction device 1505 may also be positioned so as to evacuate gastric secretions that may otherwise spread to the lungs of a patient.

Figure 16:
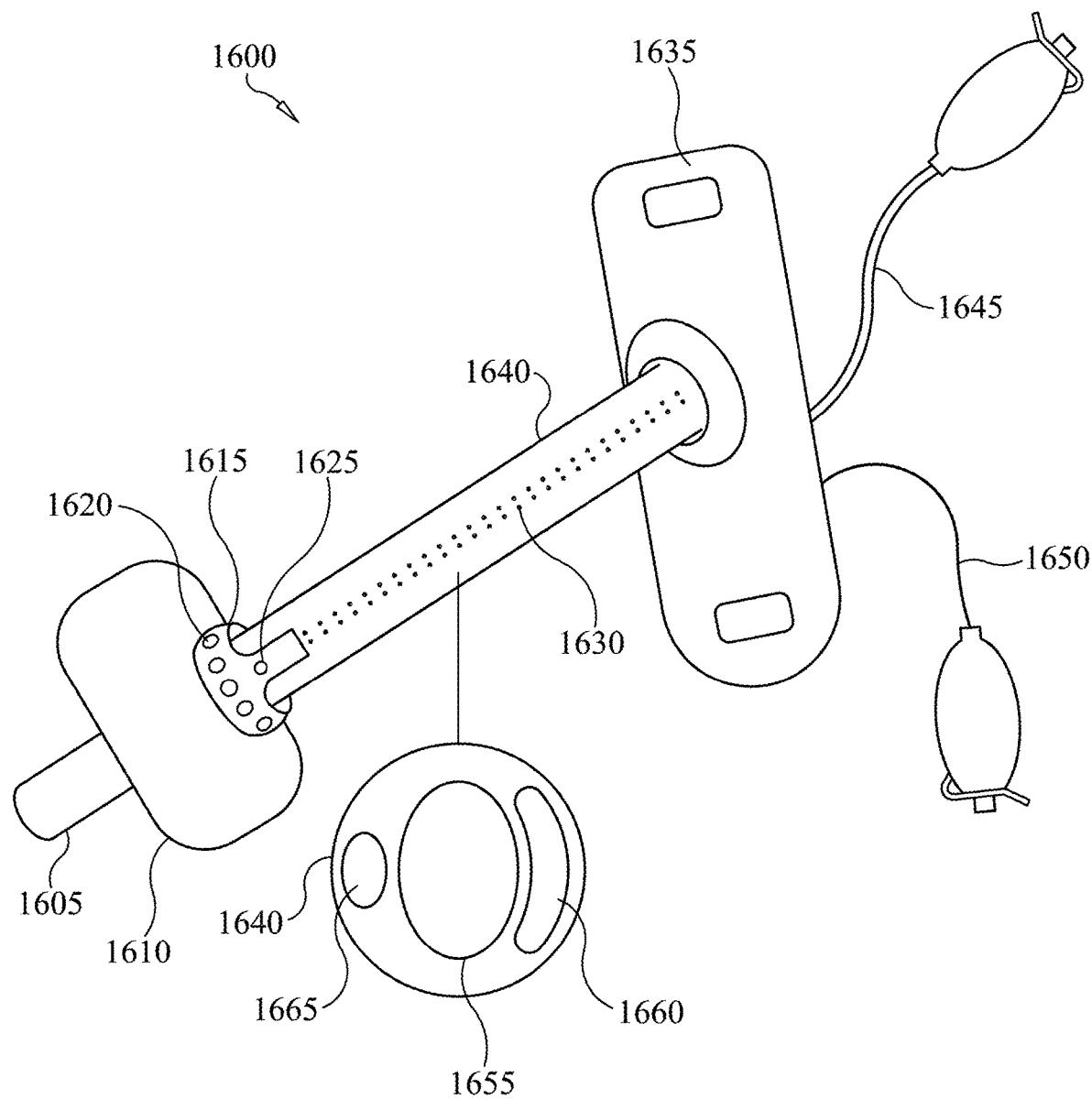
FIG. 16 shows first exemplary tracheostomy tube system, consistent with an embodiment of the present invention.
Figure 17:
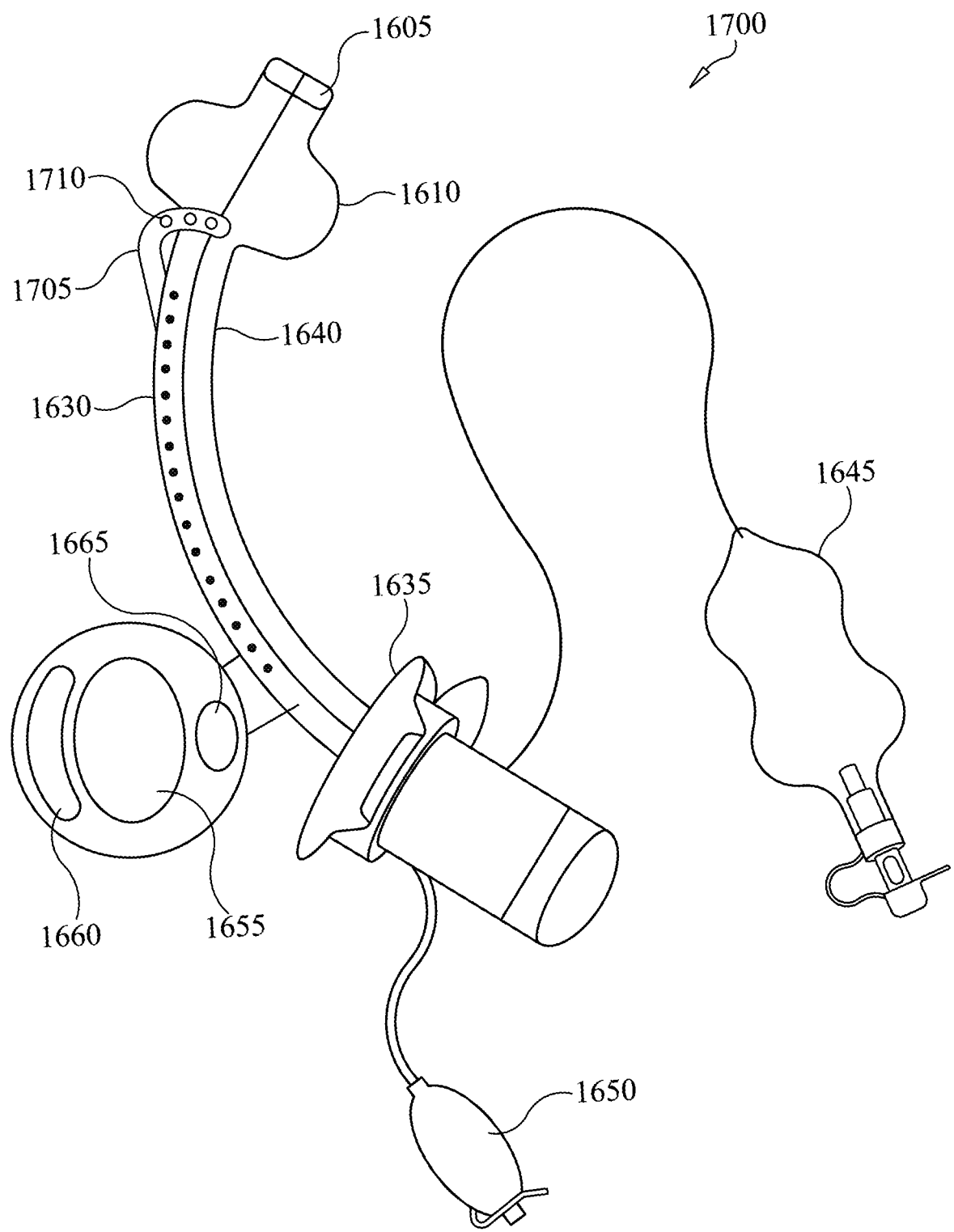
FIG. 17 shows second exemplary tracheostomy tube system, consistent with an embodiment of the present invention.

FIGS. 16 and 17 show exemplary tracheostomy tube systems 1600 and 1700, respectively, that include suction devices. More particularly, FIG. 16 provides a side perspective view of tracheostomy tube system 1600 and a cross section of a tube 1640 thereof. Tracheostomy tube system 1600 includes tube 1640 with a first end 1605, an inflatable balloon 1610, a suction device 1615 that includes a plurality of holes 1620, a suction device extension 1625, a suction line 1630, a bracket 1635, an external suction line 1645, an inflation line 1650. As may be seen in the cross-section of tube 1640 provided by FIG. 16, tube 1640 includes a tube lumen 1655, a suction line lumen 1660, and an inflation line lumen 1665.

Suction device 1615, which may have one or more features in common with the suction devices discussed above, includes one or more openings or holes 1620 and a suction line extension 1625 adapted to couple to a suction line 1630 resident within and/or coupled to tube 1640. Suction line 1630 may run the length of tube 1640 and may be coupled to and/or transition into external suction line 1645 which may be adapted to couple to a source of negative pressure (not shown), such as a vacuum pump. Inflatable balloon 1610 may be coupled to inflation line 1650, which may be adapted to couple to an air or other gas source (not shown) for the purpose of inflating and/or deflating inflatable balloon 1610.

Suction device 1615 may be any size and shape appropriate for tracheostomy tube system 1600. Exemplary shapes for suction device 1615 include circular-, semi-circular-, linear-, and/or rectangular-type shapes. In some instances, suction device 1615 may wrap completely (i.e. 360°), or partially (e.g., 90°, 180°, or 270°), around tube 1640 and/or inflatable balloon 1610. In some instances, suction device 1615 may be coincident with and/or positioned on an exterior surface of inflatable balloon 1610. In some embodiments, suction device 1615 may be coincident with a junction between inflatable balloon 1610 and tube 1640. Additionally, or alternatively, suction device 1615 may wrap around inflatable balloon 1610 and/or tube 1640 more than once in, for example, a spiral or circular concentrically placed fashion. Also, it should be noted that while only one suction device 1615 is shown in FIG. 16, this need not be the case. For example, tracheostomy tube system 1600 may employ two or more suction devices 1310.

Suction device 1615 and/or suction line extension 1625 may be made from a flexible (e.g., silicon) material and/or a rigid material (e.g., plastic). In some instances, suction line extension 1625 may be made from the same material as suction device 1615 and, in other instances, it may be made from a different material. Suction line extension 1625 may attach to suction line 1630 via, for example, a mechanical, chemical, and/or thermo bonding method. In most instances, suction device 1615 includes a lumen (not shown) that gas, liquids, and/or solids may pass through upon, for example, the application of negative pressure from a negative pressure source (e.g., a vacuum pump) coupled to suction line 1630 and/or external suction line 1645. The gas, liquids, and/or solids may enter the lumen of suction device 1615 by way of one or more of the holes 1620.

When tracheostomy tube system 1600 is in a patient, suction device 1615 may used to evacuate bodily fluids (e.g., saliva) by the application of negative pressure to holes 1620 using suction line 1630 and external suction line 1645. In this way, pools or other collections of secretions may be removed from the body on a continuous, periodic, and/or as-needed basis by being sucked into the openings or holes 1620 and evacuated from the field via the lumen of suction line 1630.

Tracheostomy tube system 1700 is similar to tracheostomy tube system 1600 with the exception that suction device 1705 is shaped as a tube that wraps around a portion of tube 1640 and/or inflatable balloon 1610. In the embodiment of FIG. 17, the suction device 1705 is a tube with one closed end that includes a multiplicity of holes and is coupled to and/or is an extension of a suction line 1630. In various embodiments, suction device 1705 may wrap partially or completely around tube 1640 and, in some instances, may wrap around tube 1640 more than once in, for example, a spiral-like pattern. In this way, pools or other collections of secretions may be removed from the body on a continuous, periodic, and/or as-needed basis by being sucked into the openings or holes 1620 and evacuated from the field via the lumen of suction line 1630.

One or more of the suction devices, or portions thereof, disclosed herein may include a material that makes the suction device/portion thereof visible to an external imaging techniques such as an X-ray, PET scan, CT scan, and/or MRI scan. In some instances, this material may be a radio-opaque marker, radioactive die, or other material (e.g., barium sulfate) that is visible/discernable when imaged. This may make the suction device and/or a medical device the suction device is coupled to easier to place within a patient and may allow a healthcare worker (e.g., doctor or nurse) to verify that the suction device and/or medical device the suction device is coupled to is properly positioned within the patient and/or working properly.

Additionally, or alternatively, one or more of the suction devices, or portions thereof, disclosed herein may include an antimicrobial material (e.g., an antibiotic) as, for example, a coating or component of the material comprising the suction device (as, e.g., a leachable agent). Additionally, or alternatively, one or more of the suction devices, or portions thereof, disclosed herein may include a leachable chemical such as a medication (e.g., an anti-inflammatory drug) as, for example, a coating or component of the material comprising the suction device.

Additionally, or alternatively, one or more of the suction devices, or portions thereof, disclosed herein may include one or more mechanisms to facilitate easy placement of the suction device and/or medical device system to which the suction device is coupled and/or prevent adhesion of a patient's tissue to the suction device. For example, a suction device may be made out of a material (e.g., silicon) so that it has a smooth exterior surface and/or may be coated with a material (e.g., TEFLON™ or lubricant) that provides a smooth and/or non-stick surface that may inhibit irritation and/or adhesion of a patient's tissue while being inserted into the patient and/or while resident within the patient.

The suction devices disclosed herein may be configured in a variety of shapes and sizes. At times, one or more dimensions of a particular suction device may be responsive to, for example, a shape or size of a medical device to which it is coupled and/or adapted to work with. For example, the suction device 100 shown in FIGS. 10-12 is sized and shaped to be coupled to tracheal tube system 101 and circumnavigate a portion (in this case, approximately 50% of the circumference) of tube 205. Thus, suction device 100 of FIGS. 10-12 is curved and semi-circular in shape. The suction devices 1310, 1415, 1505, 1615, 1705 of systems 1300, 1400, 1500, 1600, and 1700, respectively, are shaped to be responsive to a size and shape of the respective medical device system to which they are coupled.

A diameter/size of one or more of the plurality of holes included in the suction devices disclosed herein may be smaller than a diameter/size of a lumen of the respective suction device, extension, and/or suction line to which it may be coupled. For example, holes 115 may be smaller in diameter than the diameter of lumen 145, first-side lumen 130A, second-side lumen 130B, and/or a suction line lumen to which it is configured to be coupled. Having holes that are smaller than the lumen(s) prevents a solid, or semi-solid, from being sucked into a hole that could occlude, or block, a lumen of the respective suction device, extension, and/or suction line to which it may be coupled. This prevents occlusion of the lumens in a suction device and/or medical device system including a suction device and provides for proper functioning of the suction device even if one or more of the holes are blocked.

On some occasions, a suction device and/or a component thereof (e.g., an extension) may be invaginated into a suction line or component of a medical device to which it is coupled so as to, for example, minimize the profile of the suction device or component thereof so that it does not substantially protrude from an exterior surface of the suction device and/or medical device to which it is coupled.

In many instances, the size and placement of the holes in a suction device will act to increase the area of the patient's tissue across which negative pressure, or suction, is applied. This acts to reduce the pressure applied to the patient's tissue and, thereby reduce trauma to the tissue when compared with other suction devices that have only one opening via which to apply negative pressure. Because the area across which the negative pressure is applied is relatively large, a larger suction force (e.g., 100 cm $H_2O$ worth of negative pressure) may be applied to the lumen of the suction device without adverse effects to the patient's tissue. This increase in the negative pressure/suction force may act to increase the efficacy of the suction device enabling it to facilitate the evacuation of more solids and/or liquids from the patient.

In some cases, when a medical device employing a suction device is being used (e.g., inserted into a patient), the suction device may assist with the positioning and/or maintaining a position for the medical device so that, for example, the negative pressure created by the suction device may act to hold the suction device against an inner surface or wall of, for example, the trachea, larynx, surgical incision, etc. thereby preventing movement of the secretions or other substances to undesired locations within the patient (e.g., lungs, stomach, etc.).

Hence, suction devices for a tracheal tube system have been herein described.

I claim:

1. A suction device comprising:
    a suction device body including a first lumen positioned therein and a plurality of holes; and
    an extension including a second lumen positioned therein, the extension being coupled to the suction device body and configured to be inserted into a hole in a tube that includes a suction line lumen positioned within a sidewall of the tube, the hole being positioned so that when the extension is inserted into the hole, the extension forms a seal with the suction line lumen and the second lumen is in communication with the suction line lumen, an end of the suction line lumen positioned furthest away from the extension being configured for connection to a pump configured to apply a negative pressure to the first lumen, second lumen, and suction line lumen.

2. The suction device of claim 1, wherein the suction device includes a material that is visible to an imaging technique.

3. The suction device of claim 1, wherein the suction device includes an antimicrobial compound.

4. The suction device of claim 1, wherein the suction device includes a leachable chemical.

5. The suction device of claim 1, wherein the suction device is adapted to facilitate continuous or periodic application of negative pressure to tissue of a patient proximate to the suction device.

6. The suction device of claim 1, wherein the suction device body has a semi-circular shape.

7. The suction device of claim 1, wherein the extension includes a structural element configured to facilitate attachment of suction device body to the suction line.

8. The suction device of claim 1, the extension further comprising: a center structural element.

9. The suction device of claim 1, wherein the extension extends substantially orthogonally from the suction device body.

10. A medical device system comprising:
    a suction device body including a plurality of holes and a first lumen positioned therein;
    an extension including a second lumen positioned therein, the extension being coupled to the suction device body and configured to be inserted into a hole in a tube that includes a suction line lumen positioned within a sidewall of the tube, the hole being positioned so that when the extension is inserted into the hole, the extension forms a seal with the suction line lumen and the second lumen is in communication with the suction line lumen, an end of the suction line lumen positioned furthest away from the extension being configured for connection to a pump configured to apply a negative pressure to the first lumen, second lumen, and suction line lumen;
    the suction line including a third lumen and being adapted for connection to the extension on a first end so that the third lumen is in communication with the second lumen and to a pump configured to apply a negative pressure to the third lumen on a second end, the suction line being coupled to a tube; and
    the tube, the tube being flexible and hollow allowing gas to pass through.

11. The medical device system of claim 10, wherein the suction device body includes a material that is visible to an imaging technique.

12. The medical device system of claim 10, wherein the tube includes an opening adapted to accept the extension.

13. The medical device system of claim 10, further comprising: at least one of an inflatable balloon and an inflatable cuff, the suction device body being positioned proximate to the at least one inflatable balloon and inflatable cuff.

14. The medical device system of claim 13, wherein the suction device body is positioned above the at least one inflatable balloon and inflatable cuff and, when negative pressure is applied thereto, removes fluid from an area proximate to the at least one inflatable balloon and inflatable cuff.

15. The medical device system of claim 10, the extension further comprising: a center structural element.

16. The medical device system of claim 10, wherein the medical device system is adapted so that the negative pressure applied to the suction line is atraumatically applied to tissue of a patient proximate to the medical device system.

17. The medical device system of claim 10, wherein the medical device system is adapted to facilitate continuous or periodic application of negative pressure to tissue of a patient proximate to the suction device body.

* * * * *